United States Patent [19]

Johnson et al.

[11] 4,165,323

[45] Aug. 21, 1979

[54] 9-HYDROXYHEXAHYDRODIBENZO[B,D]-PYRANS, 1-SUBSTITUTED-9-HYDROXYHEXAHYDRODIBENZO[b,d]PYRANS AND INTERMEDIATES THEREFOR

[75] Inventors: Michael R. Johnson; Lawrence S. Melvin, Jr., both of Gales Ferry, Conn.

[73] Assignee: Pfizer Inc., New York, N.Y.

[21] Appl. No.: 904,192

[22] Filed: May 9, 1978

Related U.S. Application Data

[62] Division of Ser. No. 804,306, Jun. 7, 1977, Pat. No. 4,118,559.

[51] Int. Cl.$^2$ ............................................. C07D 311/42
[52] U.S. Cl. ............................... 260/345.2; 546/268; 260/345.5
[58] Field of Search ......................... 260/343.2, 343.5; 546/268

[56] References Cited

U.S. PATENT DOCUMENTS 4,118,559  10/1937  Johnson et al. ............... 260/345.2 X

OTHER PUBLICATIONS

Da Re et al., Chem. Abstracts, vol. 51, cols. 6618 to 6619 (1957).
Schonberg et al., J. Org. Chem., vol. 21, pp. 476-477 (1956).

*Primary Examiner*—John D. Randolph
*Attorney, Agent, or Firm*—Connolly and Hutz

[57] ABSTRACT

9-Hydroxyhexahydrodibenzo[b,d]pyrans, 1-substituted-9-hydroxyhexahydrodibenzo[b,d]pyrans wherein the substituent is hydrogen, methyl, hydroxymethyl, formyl, carboxy, carbamyl, amino, mono- and dialkylamino, alkanoylamino, phenalkylsulfonamido or alkylsulfonamido, and the corresponding 9-ketones, all of which are useful as CNS agents, especially as analgesics and tranquilizers, intermediates therefor and processes for their preparation.

6 Claims, No Drawings

9-HYDROXYHEXAHYDRODIBENZO[B,D]PYRANS, 1-SUBSTITUTED-9-HYDROXYHEXAHYDRODIBENZO[B,D]PYRANS AND INTERMEDIATES THEREFOR

CROSS-REFERENCE TO RELATED APPLICATION

This application is a division of application Ser. No. 804,306 filed June 7, 1977, now U.S. Pat. No. 4,118,559 granted Oct. 3, 1978.

BACKGROUND OF THE INVENTION

1. Field of the Invention

This invention relates to certain novel dibenzopyrans and, more particularly, to 9-hydroxyhexahydrodibenzo[b,d]pyrans, 1-substituted-9-hydroxyhexahydrodibenzo[b,d]pyrans wherein the substituent is hydrogen, methyl, hydroxymethyl, formyl, carboxy, carbamyl, amino, mono- or dialkylamino, alkanoylamino phenalkylsulfonamido or alkylsulfonamido, and the corresponding 9-ketones having at the 3-position an alkyl, aralkyl or pyridylalkyl, in each of which an oxygen atom can be present at some point in the alkyl moiety, or phenoxy or pyridyloxy, the use of such compounds as CNS agents, especially as tranquilizers and analgesics in mammals, including man, intermediates therefor, and processes for preparation of such compounds.

2. Description of the Prior Art

Despite the current availability of a number of analgesic agents, the search for new and improved agents continues, thus pointing to the lack of an agent useful for the control of broad levels of pain and accompanied by a minimum of side-effects. Aspirin, the most commonly used agent, is of no practical value for the control of severe pain and is known to exhibit various undesirable side-effects. Other, more potent analgesic agents such as d-propoxyphene, codeine and morphine, possess addictive liability. The need for improved and potent analgesic agents is, therefore, evident.

The preparation and analgesic properties of tetrahydro- and hexahydro-1-amino-3-alkyl-6H-dibenzo[b,d]pyrans having at the 9-position a hydrogen or a methyl group are described in U.S. Pat. No. 3,886,184, issued May 27, 1975.

Mechoulam et al., Chem. Revs., 76, 75–112 (1976) discuss several derivatives of $\Delta^1$-and $\Delta^6$-tetrahydrocannabinols which have at the 9-position a hydrogen, methyl, hydroxymethyl, formyl or carboxyl group. No references to the preparation and properties of saturated A-ring cannabinol-like compounds having such substituents at the 1-position are known.

U.S. Pat. No. 3,901,926, issued Aug. 26, 1975, describes 1-hydroxy-3-aralkyl-6,6-di(lower alkyl)-hexahydrodibenzo[b,d]pyrans having hydrogen or methyl at the 9-position which are useful as analgesic agents. U.S. Pat. Nos. 3,507,885 and 3,636,058, issued Apr. 21, 1970 and Jan. 18, 1972, respectively, describe various 1-hydroxy-3-alkyl-6H-dibenzo[b,d]pyrans having at the 9-position substituents such as oxo, hydrocarbyl and hydrocarbylidene useful as psychotropic and analgesic agents, and intermediates therefor.

Mechoulam et al., pages 129–130 in "Marijuana, Chemistry, Pharmacology and Clinical Effects", Academic Press, New York, N.Y., 1973, summarize structure-activity relationships in the cannabinoids. With respect to the 1-position, the implication is that an aromatic hydroxyl group is essential for activity. Blocking of the hydroxyl group at the 1-position as an ether group inactivates the molecule. Additionally, it is noted that introduction of a hydroxyl group on the methyl group at the 9-position retain activity. No studies appear to have been made as to the effect of substitution of groups other than hydroxyl, methyl ether or acetoxy at the 1-position.

SUMMARY OF THE INVENTION

It has now been found that certain dibenzo[b,d]pyrans; namely, 9-hydroxyhexahydro-3-substituted-6H-dibenzo[b,d]pyrans and the corresponding 9-ketone derivatives thereof (formulae I and II, respectively) are effective as CNS agents, especially as analgesics and tranquilizers, in mammals, including humans. Also included in this invention are various derivatives of said compounds which are useful as dosage forms of said compounds, and intermediates for said compounds. The compounds have the formulae:

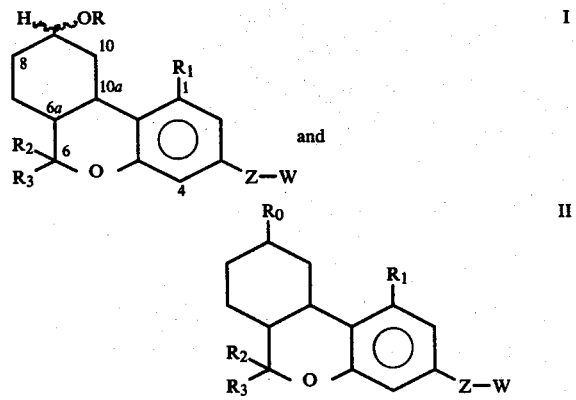

wherein
- $R_0$ is selected from the group consisting of oxo and alkylenedioxy having from two to four carbon atoms;
- OR is selected from the group consisting of hydroxy and alkanoyloxy having from one to five carbon atoms;
- $R_1$ is selected from the group consisting of hydrogen, methyl, hydroxymethyl, formyl, carboxy, carbamyl, alkylsulfonamido having from one to six carbon atoms, phenalkylsulfonamido having from one to four carbon atoms in the alkyl moiety, and $NR_4R_5$ wherein $R_4$ is selected from the group consisting of hydrogen and alkyl having from one to four carbon atoms, and $R_5$ is selected from the group consisting of $R_4$ and alkanoyl having from one to four carbon atoms, with the proviso that when $R_5$ is alkanoyl, $R_4$ is hydrogen;
- each of $R_2$ and $R_3$ is selected from the group consisting of hydrogen and methyl;
- Z is selected from the group consisting of
  - (a) alkylene having from one to ten carbon atoms;
  - (b) —$(alk_1)_m$—O—$(alk_2)_n$— wherein each of $(alk_1)$ and $(alk_2)$ is alkylene having from one to ten carbon atoms, with the proviso that the summation of carbon atoms in $(alk_1)$ plus $(alk_2)$ is not greater than ten; each of m and n is 0 or 1; and
- W is selected from the group consisting of hydrogen, pyridyl,

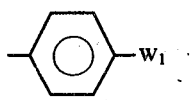

wherein $W_1$ is selected from the group consisting of hydrogen, fluoro and chloro;

and the pharmaceutically acceptable acid addition salts of those compounds wherein $R_1$ is $NR_4R_5$ and/or W is pyridyl.

For convenience, the above formulae depict the racemic compounds. However, the above formulae are considered to be generic to and embracive of the racemic modifications of the compounds of this invention, the diastereomeric mixtures, the pure enantiomers and diastereomers thereof. The utility of the racemic mixtures, the diastereomeric mixtures as well as of the pure enantiomers and diastereomers is determined by the biological evaluations described below.

Further, various intermediates useful in the preparation of compounds having the above formulae are also included in this invention. The intermediates have the formulae:

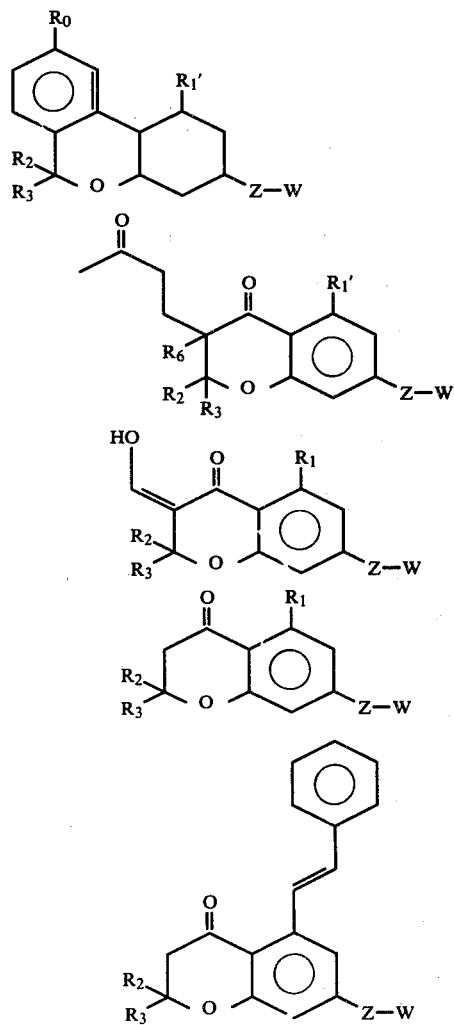

wherein each of $R_0$, $R_1$, $R_2$, $R_3$, Z and W are as defined above; $R_1'$ is hydrogen, methyl or hydroxymethyl; and $R_6$ is hydrogen or formyl.

Also included in this invention are pharmaceutically-acceptable acid addition salts of those compounds described herein which contain a basic group; i.e., those compounds wherein $R_1$ is $NR_4R_5$ and/or W is pyridyl, especially those compounds of formulae I and II having such values of $R_1$ and/or W. Representative of such salts are mineral acid salts such as the hydrochloride, hydrobromide, sulfate, nitrate, phosphate; organic acid salts such as the citrate, acetate, sulfosalicylate, tartrate, glycolate, malonate, maleate, fumarate, malate, 2-hydroxy-3-naphthoate, pamoate, salicylate, stearate, phthalate, succinate, gluconate, mandelate, lactate and methanesulfonate.

Compounds having the formula I, II and III above contain asymmetric centers at the 6a- and/or 10a-positions. There may be additional asymmetric centers in the 3-position substituent (—Z—W), and 6- and 9-positions. Diastereomers with the 9β-configuration are generally favored over the 9α-isomers because of greater (quantitatively) biological activity. For the same reason, the trans(6a,10a)diastereomers of compounds of formula I are generally favored over the cis(6a,10a)diastereomers. Among the enantiomers of a given compound one will generally be favored over the other and the racemate because of its greater activity. The enantiomer favored is determined by the procedures described herein. For convenience, the above formulae depict the racemic compounds. However, the above formulae are considered to be generic to and embracive of the racemic modifications of the compounds of this invention, the diastereomeric mixtures, the pure enantiomers and diastereomers thereof. The utility of the racemic mixtures, the diastereomeric mixtures as well as of the pure enantiomers and diastereomers is determined by the biological evaluations described below.

Asymmetric centers may exist in intermediates IV-VIII at the 2-position and in the 7-position substituent (—Z—W). The 2- and 7-positions in formulae IV-VIII correspond to the 6- and the 3-positions, respectively, of compounds having formulae I, II and III.

Favored because of their greater biological activity relative to that of other compounds described herein are compounds of formulae I and II wherein OR and $R_0$ are as defined above; $R_1$ is hydrogen, methyl, hydroxymethyl or $NR_4R_5$ wherein $R_4$ and $R_5$ are as defined above; $R_2$ is methyl; $R_3$ is hydrogen or methyl, and group —Z—W has the values shown below.

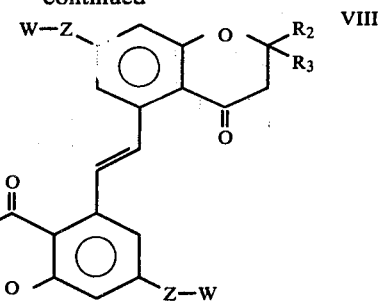

TABLE I.

| Z | W | m | n |
|---|---|---|---|
| alkylene having from 5–9 carbon atoms | H | — | — |

TABLE I.-continued

| Z | W | m | n |
|---|---|---|---|
| alkylene having from 2-5 carbon atoms | phenyl or 4-pyridyl | — | — |
| (alk$_1$)$_m$-O-(alk$_2$)$_n$ | H, phenyl | 1 | 1 |
| | H, phenyl | 0 | 1 |
| | H, phenyl | 1 | 0 |

Preferred compounds are those favored compounds designated above wherein OR is hydroxy;

$R_0$ is oxo;
$R_1$ is hydrogen, methyl, hydroxymethyl or amino;
$R_2$ is methyl;
$R_3$ is methyl;
and Z and W have the values shown below:

| Z | W | m | n |
|---|---|---|---|
| alkylene having 2-5 carbon atoms | phenyl or 4-pyridyl | — | — |
| alkylene having 5-9 carbon atoms | H | — | — |
| (alk$_1$)$_m$-O-(alk$_2$)$_n$ where (alk$_2$) is alkylene having 5-9 carbon atoms | H, phenyl | 0 | 1 |

Additionally, the favored and preferred classes of intermediates of formulae III-VIII are those compounds which serve as intermediates for the favored and preferred compounds of formulae I and II.

DETAILED DESCRIPTION OF THE INVENTION

Compounds of this invention of formulae I and II wherein $R_1$ is other than hydrogen or methyl are prepared by the following sequence (Scheme A):

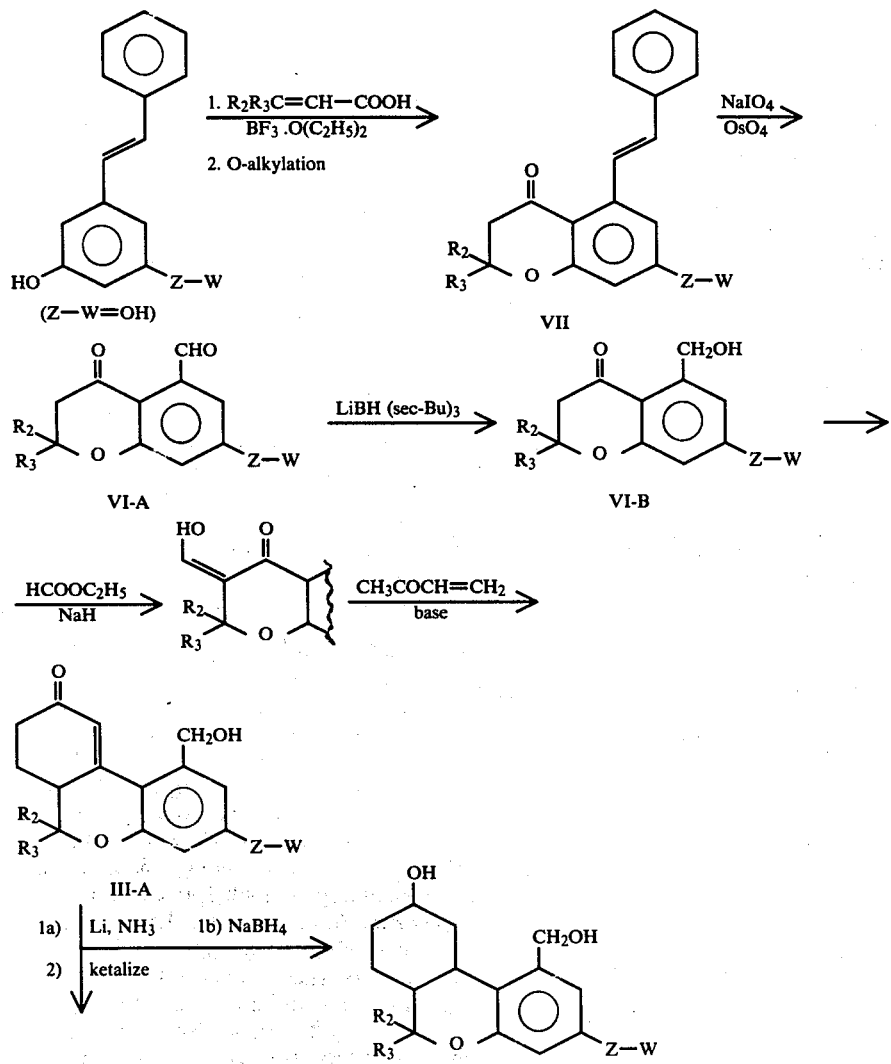

Scheme A

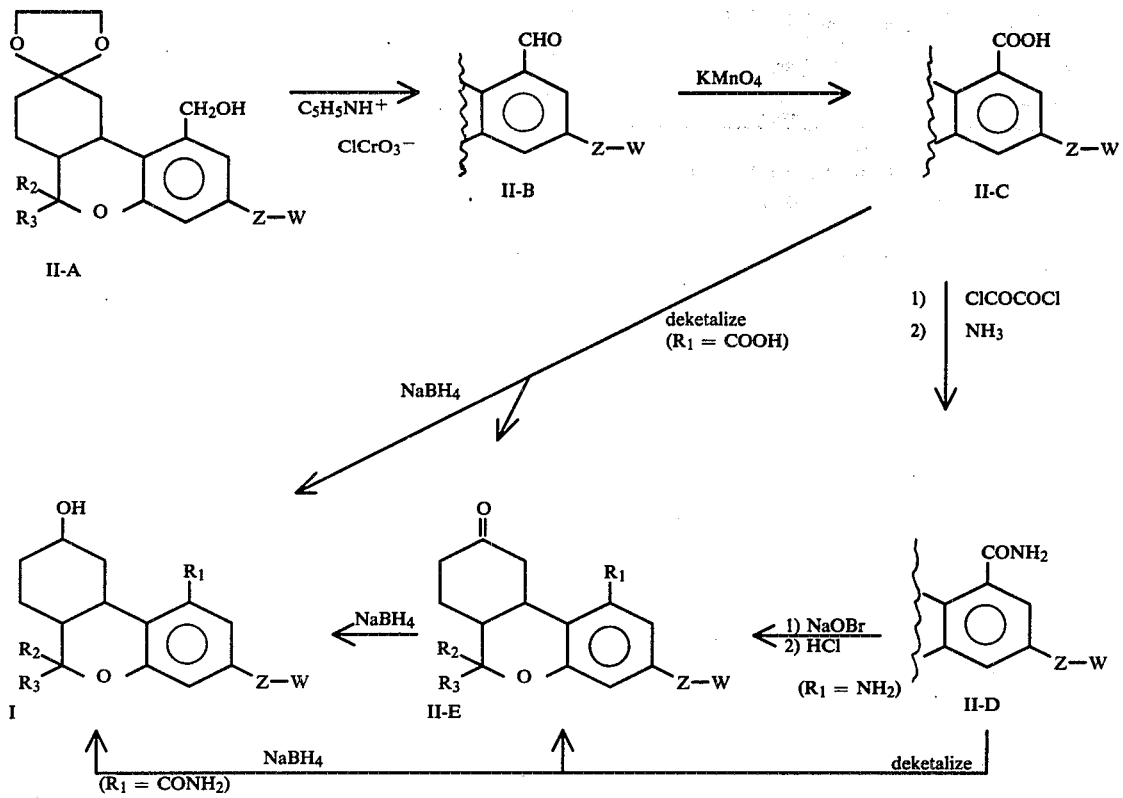

In what can be considered as one of the simpler exemplifications of the above sequence, —Z—W in the starting material represents —OH. The 3,5-dihydroxystilbene is converted to the 4-chromanone derivative of formula VII by reaction with an acrylic acid derivative of the formula $R_2R_3$-C=CH—COOH in the presence of boron trifluoride etherate at from about 20° C. to about 125° C. In addition to the 4-chromanone of formula VII a second product, isomeric to formula VII (7-$R_1'$—2,2-$R_2R_3$-5-Z-W-4-chromanone), is also produced.

When the group —Z—W represents an ether group having the formula —O—(alk$_2$)$_n$-W it is convenient to convert the 7-hydroxy (Z—W) group at this stage of the sequence. Typical procedures for ether formation comprise reaction of the 2,2-$R_2R_3$-7-hydroxy-5-(2-phenylethenyl)-4-chromanone with the mesylate or tosylate of the appropriate alcohol having the formula HO-(alk$_2$)$_n$-W in a reaction-inert solvent in the presence of a base such as an alkali metal carbonate. A suitable solvent for the reaction is N,N-dimethylformamide. The reaction is generally conducted at a somewhat elevated temperature such as, for example, at about 50° C. to about 85° C. An alternative procedure for preparing such ethers is the Williamson Synthesis which comprises reacting the 4-chromanone of formula VII in N,N-dimethylformamide with an alkali metal hydroxide, e.g. potassium hydroxide, to form the potassium salt thereof which is subsequently reacted with the appropriate bromide having the formula Br-Z-W at an elevated temperature such as, for example, from about 75° C. to about 125° C.

The compound having formula VII is then subjected to oxidation by means of sodium periodate and osmium tetroxide in a reaction-inert solvent at ambient temperatures to produce the 4-chromanone-5-carboxaldehyde having formula VI-A. The aldehyde group of formula VI-A is then converted to a hydroxymethyl group (formula VI-B) by reduction with potassium or lithium trisec-butylborohydride. Conversion of the aldehyde function to the hydroxymethyl group provides a convenient means for protecting the aldehyde function and, additionally, provides compounds having formulae I and II wherein $R_1$ is hydroxymethyl which are in themselves active as CNS agents. The 4-chromanones of formula VI-B are then converted to hydroxymethylene derivatives of formula V by reaction with methyl or ethyl formate and sodium hydride. Compounds having formula III-A are prepared by ring annelation of the appropriate 3-hydroxymethylene compounds of formula V with methyl vinyl ketone in the presence of a base; for example, an alkali metal hydroxide or alkoxide or a tertiary organic base, such as triethylamine, to effect Michael addition, followed by treatment with a base, e.g. an alkali metal hydroxide or alkoxide (sodium or potassium hydroxide, ethoxide or methoxide), to complete the cyclization.

The thus-produced 6a,7-dihydro-1-hydroxymethyl-6,6-$R_2R_3$-3-(Z-W)-6H-dibenzo[b,d]pyran-9(8H)-one (III-A) is then converted via Birch reduction to a mixture of the corresponding 6a$\beta$,7,10,10a$\alpha$-tetrahydrodibenzo[b,d]pyran-9(8H)-one and the isomeric 6a$\beta$,10a$\beta$-isomer (formula II-A). The reduction is conveniently carried out using lithium as the metal. However, sodium or potassium can also be used. The reaction is generally conducted at a temperature of from about −35° C. to about −80° C. Other methods of reduction can, of course, be used. However, the Birch reduction is favored because it offers stereoselectivity resulting in formation of the trans-ketone of formula II-A as the major product.

Treatment of compounds of formulae II and III wherein $R_0$ is oxo with the appropriate alkylene glycol having from two to four carbon atoms in the presence of a dehydrating agent such as p-toluenesulfonic acid, or other acid used in ketalization (oxalic, adipic), affords the corresponding ketals.

Reduction of the 9-oxo groups of formulae II and III compounds ($R_0$=oxo) via metal hydride reduction affords compounds of formula I (R=H). Representative of the metal hydrides useful for such conversion are lithium aluminum hydride, lithium borohydride and sodium borohydride. Sodium borohydride is favored as reducing agent in this step since it not only affords satisfactory yields of desired product, but reacts slowly enough with hydroxylic solvents (methanol, ethanol, water) to permit their use as solvents. A temperature of from about 0° C. to 30° C. is generally used. Lower temperatures, even down to about −70° C., can be used to increase selectivity of the reduction. Higher temperatures cause reaction of the sodium borohydride with the hydroxylic solvent. If higher temperatures are desired or required for a given reduction, isopropyl alcohol or the dimethyl ether of diethylene glycol are used as solvents. Agents such as lithium borohydride or lithium aluminum hydride require anhydrous conditions and non-hydroxylic solvents (1,2-dimethoxyethane, tetrahydrofuran, ether, dimethyl ether of diethylene glycol). The isomeric 9α- and 9β-hydroxy compounds are produced in this step.

When the value of the $R_1$ variable as hydroxymethyl is desired, direct conversion of formula II-A compounds to formula I compounds is achieved as described above. When, however, $R_1$ is to be other than hydroxymethyl, compounds having formula II-A are converted to corresponding carboxaldehydes having formula II-B by oxidation with the stable reagent pyridinium chloro chromate according to the procedure described in *Tetrahedron Letters*, 2647 (1975). Oxidation of the carboxaldehyde group by means of potassium permanganate affords the corresponding carboxylic acid compound of formula II-C. Treatment of the carboxylic acid compound with oxalyl chloride in the presence of a base such as sodium hydroxide followed by treatment of the thus-produced acid chloride with ammonia affords the corresponding carboxamide derivatives having formula II-D. A variety of halogenating agents other than oxalyl chloride can, of course, be used in this process to produce the acid chloride. Representative of such agents are thionyl chloride, phosphorus pentachloride or phosphorous oxychloride. The carboxamide derivatives are then converted, by treatment with sodium hypobromite, to the corresponding amino compounds which, when treated with acid, are deketalized to give compounds having formula II-E wherein $R_1$ is amino. Reduction of the 9-oxo groups by sodium borohydride, as previously described, produces the corresponding 9-hydroxy derivatives having formula I. The isomeric 9α- and 9β-hydroxy compounds are produced.

It is evident from the above reaction sequence that compounds of formula I having the various values previously ascribed to it can be produced by reduction of the 9-oxo group of the appropriate formula II compound having the desired $R_1$ value.

Compounds of formula II-B are deformylated by treatment with tristriphenylphosphine rhodium chloride, thus providing a convenient route to compounds of formulae I and II wherein $R_1$ is hydrogen. The procedure comprises refluxing the formyl compound of formula II-B with tris-triphenylphosphine rhodium chloride in a reaction-inert solvent such as toluene or other hydrocarbon having a boiling point above 75° C. for several hours until reaction is complete.

An alternative procedure to production of formula VI-A compounds comprises the reaction of 3,3',5,5'-tetrahydroxystilbene with the appropriate 3,3-$R_2R_3$-substituted acrylic acid in boron trifluoride etherate to produce the corresponding bis-(2,2-$R_2R_3$-7-hydroxy-5-methylidene-4-chromanone). This compound is then converted to ethers in the manner described above for preparation of ethers of compounds having formula VII. Oxidation of the bis(5-methylene-4-chromanone) compound by means of sodium periodate and osmium tetroxide produces compounds having formula VI-A. This reaction sequence is outlined in Scheme B below.

Scheme B

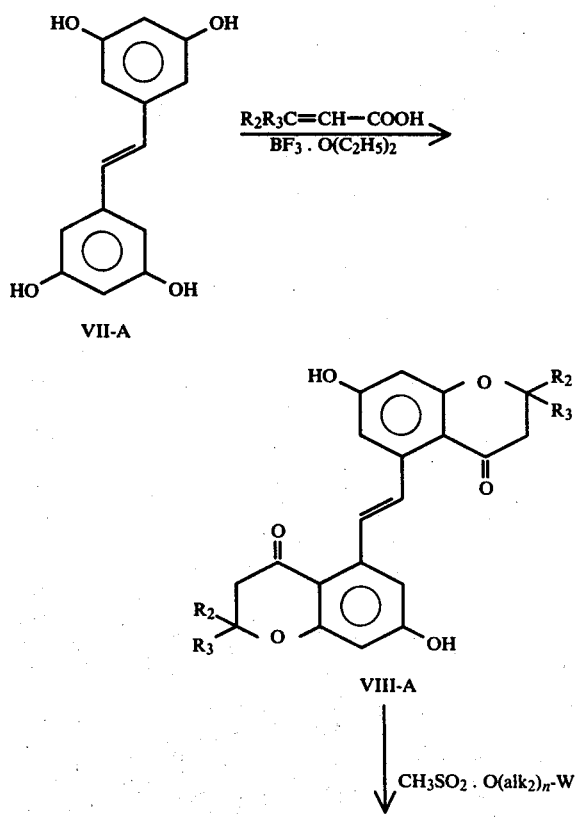

-continued

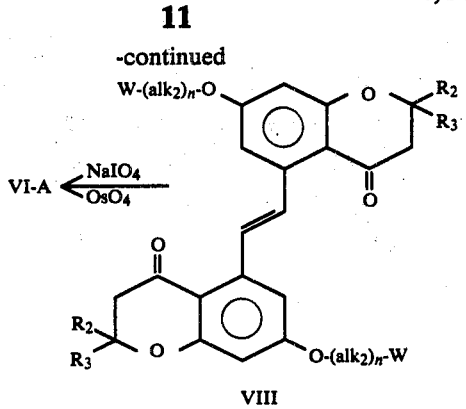

VIII

A still further procedure for producing compounds having formulae I and II wherein $R_1$ is amino comprises the reaction sequence illustrated in Scheme C.

Scheme C

II-D

*coupler = e.g. ClP(O)[N(CH$_3$)$_2$]$_2$, ClP(O)(OC$_2$H$_5$)$_2$

This sequence comprises reaction of the appropriate 6a,7,10,10a-tetrahydro-1-hydroxy-3-(Z-W)-6,6-$R_2R_3$-6H-dibenzo[b,d]pyran-9(8H)-one ethylene ketal with a coupling agent such as diethylchlorophosphate, bis(-dimethylamino)phosphorochloridate or trifluoromethanesulfonyl imidazole in the presence of a suitable base as acid acceptor. The diethyl phosphoryl or other derivative thus produced is then reacted with sodium or potassium in the presence of ferric nitrate and with ammonia to produce the corresponding amino derivative. The phosphorous containing couplers produce, in addition to the desired amino derivative, the dehydroxylated compound.

The necessary starting materials for the reaction sequence of Scheme C are known compounds described by Fahrenholtz, U.S. Pat. No. 3,636,058, issued Jan. 18, 1972; Archer, U.S. Pat. No. 3,928,598, issued Dec. 23, 1975 and in Netherlands specification 7612174, published May 5, 1977.

Compounds of this invention wherein $R_1$ is hydrogen, methyl or hydroxymethyl are prepared by the sequence of Scheme A but beginning, of course, with the appropriate 3-$R_1$-5-Z-W phenol. The required starting materials are prepared according to reaction Scheme D ($R_1''$=H, CH$_3$, 2-phenylethenyl).

Scheme D

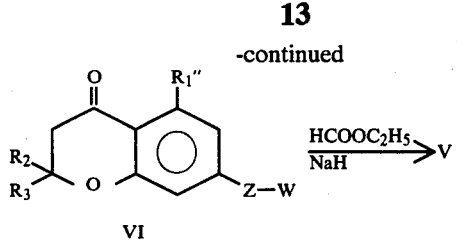

VI

The starting 3-hydroxy-5-$R_1''$ benzoic acid (IX) is converted to a compound of formula X wherein $Y_2$ represents an alkoxy group, desirably methoxy or ethoxy for ease of preparation, or an amino group; and $Y_1$ is a hydroxy protecting group, by methods described in the literature.

When Z is alkylene, $Y_1$ is desirably alkyl having from one to four carbon atoms or benzyl. The function of group $Y_1$ is to protect the hydroxy groups during subsequent reactions. It is its ability to perform a specific function; i.e. protection of the hydroxy groups, rather than its structure which is important. The selection and identification of appropriate protecting groups can easily and readily be made by one skilled in the art. The suitability and effectiveness of a group as a hydroxy protecting group are determined by employing such a group in the above-illustrated reaction sequence. It should, therefore, be a group which is easily removed to permit restoration of the hydroxy groups. Methyl is favored as a protecting alkyl group since it is easily removed by treatment with pyridine hydrochloride. The benzyl group, if used as a protecting group, is removed by catalytic hydrogenolysis or acid hydrolysis.

When Z is -(alk$_1$)$_m$-O-(alk$_2$)$_n$—, $Y_1$ is preferably benzyl or a substituted benzyl group since it can subsequently be removed without detriment to the Z group.

The protected benzoic acid derivative (X) is then converted to a compound of formula XII by known technology. In one procedure, X is hydrolyzed to the corresponding acid ($Y_2$=OH), or lithium salt, and reacted with the appropriate alkyl lithium to produce a substituted phenyl ketone ($Y_2$=alkyl). When methyl lithium is used, the resulting acetophenone derivative is treated with a Grignard Reagent (W-Z'-MgBr) where $Z'$=Z less one $CH_2$ group. The intermediate adduct is hydrolyzed to the corresponding alcohol which is then hydrogenolyzed to replace the hydroxy group with hydrogen. This procedure is especially useful for those compounds wherein Z is alkylene.

The ether group (or groups) are deblocked by suitable means: treatment with pyridine hydrochloride ($Y_1$=methyl) or catalytic hydrogenolysis ($Y_1$=benzyl), or by treatment with an acid such as trifluoroacetic acid, hydrochloric, hydrobromic or sulfuric acids, or pyridine hydrochloride.

A further method for converting compounds of formula X to those of formula XI comprises reaction of a ketone of formula X ($Y_2$=alkyl) with the appropriate triphenyl phosphonium bromide derivative [($C_6H_5$)$_3$P+-Z-W]Br$^-$ in the presence of a base (e.g. sodium hydride). The reaction proceeds via an alkene which is subsequently catalytically hydrogenated to the corresponding alkane (Z-W) and deblocked to provide compound XII. Of course, when -Z- is (alk$_1$)$_m$-O-(alk$_2$)$_n$ and $Y_1$ is benzyl, the catalytic hydrogenation also results in cleavage of the benzyl ethers.

Alternatively, conversion of formula X compounds to those of structure XII can be achieved by the sequence X→XI→XII. In this sequence, the diprotected benzamide (formula X, $Y_2$=NH$_2$) is converted to the ketone (XI, Z'=Z less one $CH_2$ group) by reaction with the appropriate Grignard reagent (BrMg-Z'-W) followed by reaction with methyl- or ethyl-magnesium halide to form the corresponding carbinol. Dehydration of the carbinol, e.g. with p-toluenesulfonic acid, affords the corresponding alkene which is then catalytically hydrogenated (Pd/C) to the alkane (XII). Any ether groups present are deblocked (converted to hydroxy) as described above.

The conversion of XII to the 4-chromanone VI is achieved by the reaction of XII with an acrylic acid of the formula $R_2R_3$-C=CH-COOH as is described above.

Compounds of formula XII wherein -Z-W is -alkylene-W or -(alk$_1$)-O—(alk$_2$)$_n$-W wherein (alk$_1$), (alk$_2$), W, $R_1''$ and n are as defined above are obtained by the Scheme E:

Scheme E

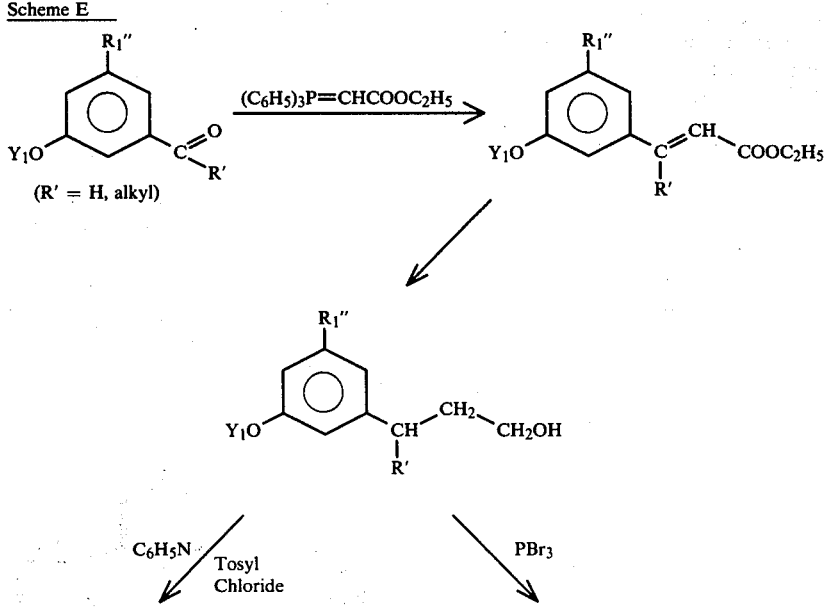

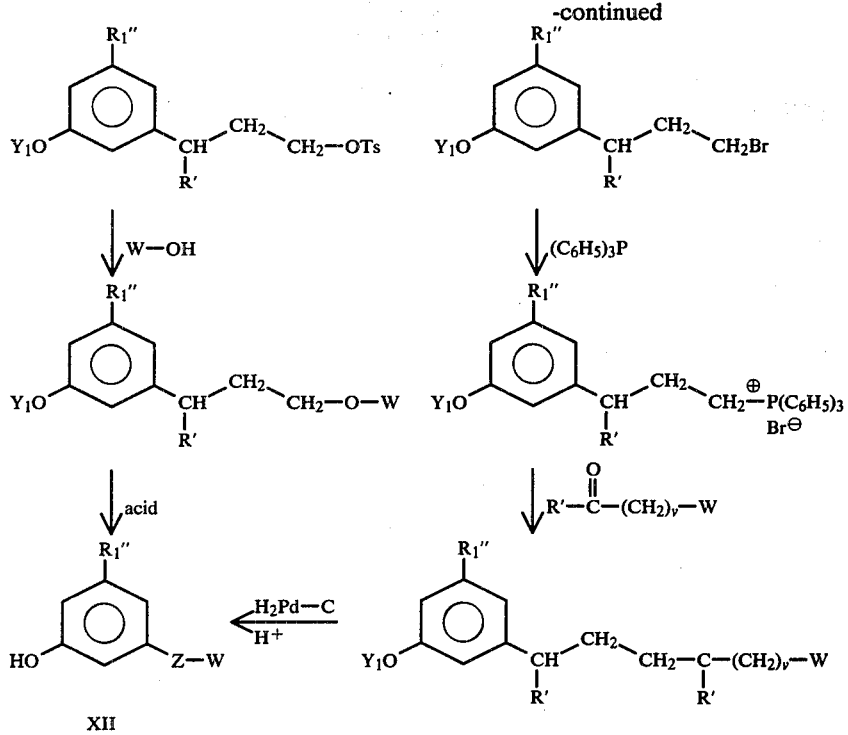

The first step in the above sequence (the Wittig reaction) provides opportunity, by choice of appropriate reactants, to produce compounds having straight or branched alkylene groups. In the given illustration, the value of R' as methyl or ethyl permits formation of a compound having alkyl substitution on the carbon atom ($\alpha$) adjacent to the phenyl group. Substitution of a methyl or ethyl group at other sites, e.g. the $\beta$-carbon atom of the alkylene group, is achieved by choice of the appropriate carbalkoxy alkylidene triphenylphosphorane, e.g. $(C_6H_5)_3P=C(R')-COOC_2H_5$. The unsaturated ester thus produced is reduced to the corresponding saturated alcohol by reaction with lithium aluminum hydride.

Alternatively, when $Y_1$ is other than benzyl (e.g. methyl), the alcohol is produced by catalytic reduction of the unsaturated ester using palladium-carbon, followed by treatment of the saturated ester thus produced with lithium aluminum hydride. Conversion of the alcohol to the corresponding tosylate or mesylate followed by alkylation of the tosylate or mesylate with an alkali metal salt of the appropriate HO-(alk$_2$)-W reactant, and finally removal of the protecting group ($Y_1$) affords the desired resorcinol.

A variation of the above sequence comprises bromination of the alcohol rather than converting it to a tosylate or mesylate. Phosphorous tribromide is a convenient brominating agent. The bromo derivative is then reacted with the appropriate HO-(alk$_2$)-W in the presence of a suitable base (Williamson synthesis).

The bromo compounds also serve as valuable intermediates for increasing the chain length of the alkylene moiety in the above sequence to give compounds wherein Z is -alkylene-W. The process comprises treating the bromo derivative with triphenyl phosphine to produce the corresponding triphenylphosphonium bromide. Reaction of the triphenylphosphonium bromide with the appropriate aldehyde or ketone in the presence of a base such as sodium hydride or n-butyl lithium affords an unsaturated derivative which is then catalytically hydrogenated to the corresponding saturated compound.

In this variation, the value of the protecting group ($Y_1$) selected depends upon the particular sequence followed. When the vertical sequence on the right is used, benzyl is the preferred protecting group by reason of the catalytic hydrogenation step. Methyl is the preferred protecting group when the left vertical sequence is followed, since it is conveniently removed by treatment with acid as described herein.

A further method for making compounds of formula XII wherein Z-W is (alk$_1$)-O-(alk$_2$)-W comprises reaction of the appropriate 3-(protected hydroxy)-5-R$_1$'-styrene oxide with an alcohol [HO-(alk$_2$)-W] as its alkali metal (preferably sodium or potassium) salt. Benzyl is a favored protecting group because of its ease of removal. The resulting ether compound (formula XII-A) is converted to the corresponding alkyl ether (formula XIII-B) by treatment with phosphorous oxychloride. The thus-produced olefinic mixture is reduced with hydrogen over palladium. Removal of the protecting groups as described above affords the desired compound. The reaction sequence is presented below ($Y_1$=benzyl, alkyl having one to four carbon atoms; R'=H, CH$_3$, C$_2$H$_5$ and may be alike or different); R$_1$" is H, CH$_3$ or 2-phenylethenyl.

Scheme F

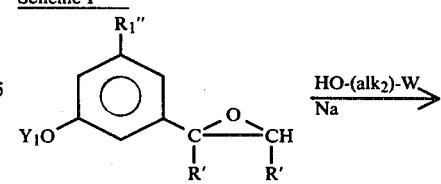

-continued

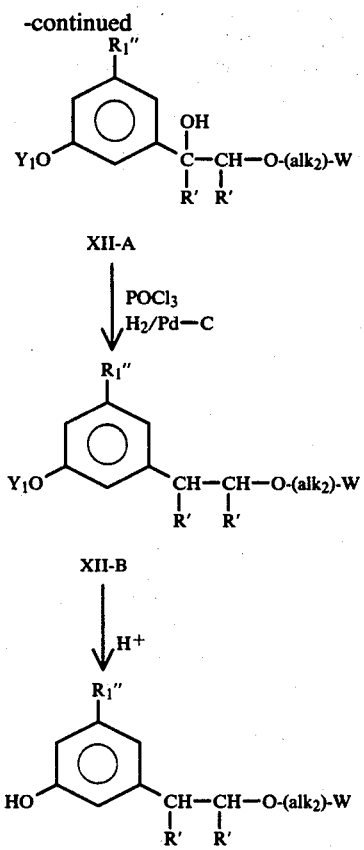

Similarly, 1-Z-W-5-methoxy-3-stilbene derivatives are prepared from the appropriate 5-methoxy-3-stilbene carboxylic acid methyl ester. Removal of the protective methyl group is achieved by treatment with pyridine hydrochloride. The thus produced 5-hydroxy-3-stilbene derivative is then converted to the corresponding 4-chromanone by the above described procedures.

Esters of formula I compounds in which the OR group is esterified are prepared by acylation with the appropriate alkanoic acid in the presence of a condensing agent such as dicyclohexylcarbodiimide or by reaction with the appropriate alkanoic acid chloride or anhydride, e.g. acetyl chloride or acetic anhydride, in the presence of a base such as pyridine. Formula I compounds wherein $R_1$ is amino in which only the 1-amino group is acylated are obtained by borohydride reduction of the corresponding formula II ketone acylated at the 1-position. The thus-produced formula I compounds bearing 1-acylamido-9-hydroxy substitution can then be acylated further with a different acylating agent to produce a diacylated compound of formula I in which the acyl groups at the 1- and the 9-positions are different. Acylation of formula I compounds wherein $R_1$ is amino and OR is OH according to the above-described procedures affords diacyl derivatives wherein the acyl groups on the 1-amino and 9-hydroxy groups are alike.

Compounds of formula II-E in their ketalized form serve as valuable intermediates for preparation of compounds wherein $R_1$ is $-NR_4'R_5$, wherein $R_4'$ is alkyl and $R_5$ is as previously defined, by reductive alkylation according to known procedures, e.g. using the appropriate aldehyde and sodium cyanoborohydride; and for compounds wherein $R_1$ is alkylsulfonamido or phenalkylsulfonamido by chlorosulfonamidation according to known methods; i.e., in a reaction-inert solvent in the presence of an acid acceptor at from $-20°$ C. to $50°$ C.

Additionally, the amino group can be converted by known procedures to the diazonium group which in turn can be replaced with or converted to a variety of groups via known methodology, e.g. chloro, fluoro, cyano, bromo, iodo and mercapto. The said derivatives have the same utility as the compounds of formulae I and II described herein and are used in the same manner.

The analgesic properties of the compounds of this invention are determined by tests using nociceptive stimuli.

Tests Using Thermal Nociceptive Stimuli (a) Mouse Hot Plate Analgesic Testing (HP)

The method used is modified after Woolfe and MacDonald, J. Pharmacol. Exp. Ther., 80, 300–307 (1944). A controlled heat stimulus is applied to the feet of mice on a ⅛″ thick aluminum plate. A 250 watt reflector infrared heat lamp is placed under the bottom of the aluminum plate. A thermal regulator, connected to thermistors on the plate surface, programs the heat lamp to maintain a constant temperature of 57° C. Each mouse is dropped into a glass cylinder (6½″ diameter) resting on the hot plate, and timing is begun when the animal's feet touch the plate. The mouse is observed at 0.5 and 2 hours after treatment with the test compound for the first "flicking" movements of one or both hind feet, or until 10 seconds elapse without such movements. Morphine has an $MPE_{50}=4$–5.6 mg./kg. (s.c.).

(b) Mouse Tail Flick Analgesic Testing (TF)

Tail flick testing in mice is modified after D'Amour and Smith, J. Pharmacol. Exp. Ther., 72, 74–79 (1941), using controlled high intensity heat applied to the tail. Each mouse is placed in a snug-fitting metal cylinder, with the tail protruding through one end. This cylinder is arranged so that the tail lies flat over a concealed heat lamp. At the onset of testing, an aluminum flag over the lamp is drawn back, allowing the light beam to pass through the slit and focus onto the end of the tail. A timer is simultaneously activated. The latency of a sudden flick of the tail is ascertained. Untreated mice usually react within 3–4 seconds after exposure to the lamp. The end point for protection is 10 seconds. Each mouse is tested at 0.5 and 2 hours after treatment with morphine and the test compound. Morphine has an $MPE_{50}$ of 3.2–5.6 mg./kg. (s.c.).

(c) Tail Immersion Procedure (TI)

The method is a modification of the receptacle procedure developed by Benbasset, et al., Arch. int. Pharmacodyn., 122, 434 (1959). Male albino mice (19–21 g.) of the Charles River CD-1 strain are weighed and marked for identification. Five animals are normally used in each drug treatment group with each animal serving as its own control. For general screening purposes, new test agents are first administered at a dose of 56 mg./kg. intraperitoneally or subcutaneously, delivered in a volume of 10 ml./kg. Preceding drug treatment and at 0.5 and 2 hours post drug, each animal is placed in the cylinder. Each cylinder is provided with holes to allow for adequate ventilation and is closed by a round nylon plug through which the animal's tail protrudes. The cylinder is held in an upright position and the tail is completely immersed in the constant temperature waterbath (56° C.). The endpoint for each trial is an energetic jerk or twitch of the tail coupled with a motor response. In some cases, the endpoint may be less vigorous post drug. To prevent undue tissue damage, the trial is terminated and the tail removed from the waterbath within 10 seconds. The response latency is recorded in seconds to the nearest 0.5 second. A vehicle control and a standard of known potency are tested concurrently with screening candidates. If the activity of a test agent has not returned to baseline values at the 2-hour testing point, response latencies are determined at 4 and 6 hours. A final measurement is made at 24 hours if activity is still observed at the end of the test day.

Test Using Chemical Nociceptive Stimuli

Suppression of Phenylbenzoquinone Irritant-Induced Writhing (PBQ)

Groups of 5 Carworth Farms CF-1 mice are pretreated subcutaneously (SC) or orally (PO) with saline, morphine, codeine or the test compound. Twenty minutes (if treated subcutaneously) or fifty minutes (if treated orally) later, each group is treated with intraperitoneal injection of phenylbenzoquinone, an irritant known to produce abdominal contractions. The mice are observed for 5 minutes for the presence or absence of writhing starting 5 minutes after the injection of the irritant. $ED_{50}$'s or $MPE_{50}$'s of the drug pretreatments in blocking writhing are ascertained.

Tests Using Pressure Nociceptive Stimuli

Effect on the Haffner Tail Pinch Procedure (Rat Tail Clamp, RTC)

A modification of the procedure of Haffner, Experimentelle Prufung Schmerzstillender. Mittel Deutch Med. Wschr., 55, 731–732 (1929) is used to ascertain the effects of the test compound on aggressive attacking responses elicited by a stimulus pinching the tail. Male albino rats (50–60 g.) of the Charles River (Sprague-Dawley) CD strain are used. Prior to drug treatment, and again at 0.5, 1, 2 and 3 hours after treatment, a Johns Hopkins 2.5-inch "bulldog" clamp is clamped onto the root of the rat's tail. The endpoint at each trial is clear attacking and biting behavior directed toward the offending stimulus, with the latency for attack recorded in seconds. The clamp is removed in 30 seconds if attacking has not yet occurred, and the latency of response is recorded as 30 seconds. Morphine is active at 17.8 mg./kg. (i.p.).

Tests Using Electrical Nociceptive Stimuli

The "Flinch-Jump" Test (FJ)

A modification of the flinch-jump procedure of Tenen, Psychopharmacologia, 12, 278–285 (1968) is used for determining pain thresholds. Male albino rats (175–200 g.) of the Charles River (Sprague-Dawley) CD strain are used. Prior to receiving the drug, the feet of each rat are dipped into a 20% glycerol/saline solution. The animals are then placed in a chamber and presented with a series of 1-second shocks to the feet which are delivered in increasing intensity at 30-second intervals. These intensities are 0.26, 0.39, 0.52, 0.78, 1.05, 1.31, 1.58, 1.86, 2.13, 2.42, 2.72 and 3.04 mA. Each animal's behavior is rated for the presence of (a) flinch, (b) squeak and (c) jump or rapid forward movement at shock onset. Single upward series of shock intensities are presented to each rat just prior to, and at 0.5, 2, 4 and 24 hours subsequent to drug treatment.

Results of the above tests are recorded as the effective dose which protects 50% of the animals tested ($ED_{50}$) against the nociceptive stimuli during the test period or as percent maximum possible effect (% MPE). The % MPE of each group is statistically compared to the % MPE of the standard and the predrug control values. The % MPE is calculated as follows:

$$\% MPE = \frac{\text{test time} - \text{control time}}{\text{cutoff time} - \text{control time}} \times 100$$

The compounds of the present invention are active analgesics via oral and parenteral administration and are conveniently administered in composition form. Such compositions include a pharmaceutical carrier selected on the basis of the chosen route of administration and standard pharmaceutical practice. For example, they may be administered in the form of tablets, pills, powders or granules containing such excipients as starch, milk sugar, certain types of clay, etc. They may be administered in capsules, in admixtures with the same or equivalent excipients. They may also be administered in the form of oral suspensions, solutions, emulsions, syrups and elixirs which may contain flavoring and coloring agents. For oral administration of the therapeutic agents of this invention, tablets or capsules containing from about 0.01 to about 100 mg. are suitable for most applications.

The physician will determine the dosage which will be most suitable for an individual patient and it will vary with the age, weight and response of the particular patient and the route of administration. Generally, however, the initial analgesic dosage in adults may range from 0.01 to 500 mg. per day in single or divided doses. In many instances, it is not necessary to exceed 100 mg. daily. The favored oral dosage range is from about 0.01 to about 300 mg./day; the preferred range is from about 0.10 to about 100 mg./day. The favored parenteral dose is from about 0.01 to about 100 mg./day; the preferred range from about 0.01 to about 50 mg./day.

EXAMPLE 1

2,2-Dimethyl-7-hydroxy-5-(2-phenylethenyl)-4-chromanone

A 25° C. mixture of 30.0 g. (0.142 mole) of 3,5-dihydroxystilbene and 18.4 g. (0.184 mole) of 3,3-dimethylacrylic acid in 75 ml. (0.609 mole) of borontrifluoride etherate is stirred for 40 hours. The reaction is slowly diluted with 150 ml. of water and then with 330 ml. of 6N sodium hydroxide. The resultant mixture is heated on a steam bath for 10 minutes followed by cooling in ice and acidification with 150 ml. of concentrated hydrochloric acid. The reaction mixture is extracted twice with 500 ml. portions of ethyl acetate. The extracts are combined, washed twice with 500 ml. portions of saturated sodium bicarbonate and dried over magnesium sulfate. The extract is concentrated under reduced pressure to 300 ml. volume and the concentrate allowed to crystallize yielding 21.8 g. (52.3%) of 2,2-dimethyl-7-hydroxy-5-(2-phenylethenyl)-4-chromanone. The mother liquor is purified via column chromatography on silica gel eluted with 50% ether-hexane to yield another 3.85 g. (9.2%) of product and 9.2 g. (22%) of 2,2-dimethyl-5-hydroxy-7-(2-phenylethenyl)-4-chromanone.

2,2-Dimethyl-7-hydroxy-5-(2-phenylethenyl)-4-chromanone:

M.P.: 221° L C. (from ether-ethyl acetate)

IR: (KBr) 1642, 1623, 1597 and 1575 cm$^{-1}$.

UV: $\lambda_{max}^{95\% \ ethanol}$ ($\epsilon$) 271 (61,200) and 317 (31,500) nm.

PMR: $\delta_{D6\text{-}DMSO}^{TMS}$ 1.33 (s, C-2 methyls), 2.66 (s, methylene), 6.25 (d, J=2 Hz, C-8 ArH), 6.68 (d, J=2 Hz, C-6 ArH), 6.93 (d, J=16 Hz, vinyl proton), 7.17-7.57 (m, PhH) and 8.12 (d, J=16 Hz, vinyl proton).

MS: 294 (M+), 279, 239 and 238.

Analysis: Calc'd for $C_{19}H_{18}O_3$: C, 77.53; H, 6.16%; Found: C, 77.09; H, 6.15%.

2,2-Dimethyl-5-hydroxy-7-(2-phenylethenyl)-4-chromanone:

M.P.: 116° C. (from hexane)

PMR: $\delta_{CDCl_3}^{TMS}$ 1.48 (s, C-2 methyls), 2.75 (s, methylene), 6.55 (d, J=2 Hz, C-8 ArH), 6.62 (d, J=2 Hz, C-6 ArH) and 7.0-7.6 (m, vinyl and PhH).

Analysis: Calc'd for $C_{19}H_{18}O_3$: C, 77.53; H, 6.16%; Found: C, 77.39; H, 6.15%.

In like manner, the following compounds are prepared from the appropriate stilbene and the appropriate acrylic acid reactant of the formula $R_2R_3C=CH\text{-}COOH$.

| $R_2$ | $R_3$ | Z | W |
|---|---|---|---|
| H | H | O | H |
| H | $CH_3$ | O | H |
| $CH_3$ | $CH_3$ | $(CH_2)_3$ | H |
| $CH_3$ | $CH_3$ | $C(CH_3)_2(CH_2)_6$ | H |
| $CH_3$ | $CH_3$ | $CH(CH_3)CH(CH_3)(CH_2)_5$ | H |
| H | $CH_3$ | $C(CH_3)_2(CH_2)_6$ | H |
| $CH_3$ | H | $(CH_2)_{10}$ | H |
| $CH_3$ | $CH_3$ | $CH(CH_3)(CH_2)_3$ | $C_6H_5$ |
| H | $CH_3$ | $CH(CH_3)(CH_2)_3$ | $4\text{-}FC_6H_4$ |
| $CH_3$ | $CH_3$ | $CH(CH_3)(CH_2)_3$ | 4-pyridyl |
| $CH_3$ | $CH_3$ | $(CH_2)_8$ | $C_6H_5$ |
| H | $CH_3$ | $C(CH_3)_2(CH_2)_6$ | $4\text{-}ClC_6H_4$ |
| H | H | $CH(CH_3)(CH_2)_2CH(CH_3)$ | $C_6H_5$ |
| $CH_3$ | $CH_3$ | $(CH_2)_3\text{—}O\text{—}$ | $C_6H_5$ |
| H | H | $(CH_2)_4\text{—}O\text{—}CH_2$ | $4\text{-}FC_6H_4$ |
| H | $CH_3$ | $(CH_2)_3OCH(CH_3)(CH_2)_2$ | $C_6H_5$ |
| $CH_3$ | $CH_3$ | $CH(CH_3)(CH_2)_2O(CH_2)_4$ | 4-pyridyl |
| $CH_3$ | $CH_3$ | $(CH_2)_3O(CH_2)_3$ | H |
| H | $CH_3$ | $(CH_2)_3\text{—}O\text{—}$ | $4\text{-}FC_6H_4$ |
| $CH_3$ | $CH_3$ | $(CH_2)_4O$ | H |
| $CH_3$ | $CH_3$ | $(CH_2)_8O$ | $C_6H_5$ |
| $CH_3$ | $CH_3$ | $CH(C_2H_5)(CH_2)_2O$ | $C_6H_5$ |
| $CH_3$ | $CH_3$ | $OCH_2$ | $4\text{-}FC_6H_4$ |
| H | H | $CH_2$ | $4\text{-}ClC_6H_4$ |
| H | $CH_3$ | $(CH_2)_7$ | H |
| $CH_3$ | $CH_3$ | $(CH_2)_3OCH(CH_3)(CH_2)_2$ | 4-pyridyl |
| H | $CH_3$ | $CH(C_2H_5)CH_2$ | $C_6H_5$ |
| $CH_3$ | $CH_3$ | $(CH_2)_5$ | 2-pyridyl |
| $CH_3$ | $CH_3$ | $(CH_2)_5$ | H |
| $CH_3$ | $CH_3$ | $C(CH_3)_2$ | $C_6H_5$ |

The isomeric 2,2-$R_2R_3$-5-hydroxy-7-(2-phenylethenyl)-4-chromanones are also produced in each instance.

EXAMPLE 2

2,2-Dimethyl-5-(2-phenylethenyl)-7-[2-(5-phenylpentyloxy)]-4-chromanone

Method A: A mixture of 21.8 g. (74.1 mmoles) of 2,2-dimethyl-7-hydroxy-5-(2-phenylethenyl)-4-chromanone, 21.8 g. (90.0 mmole) of 2-(5-phenylpentyl)methanesulfonate and 21.8 g. (158 mmoles) anhydrous potassium carbonate in 150 ml. of dimethylformamide is heated at 85° C. for 20 hours. The reaction mixture is then cooled and added to a mixture of one liter of ether and one liter of cold water. The ether extract is washed with two 500 ml. portions of water. The total aqueous extract is extracted again with 500 ml. ether and the ether extract washed with two 250 ml. portions of water. The total combined extract is dried over magnesium sulfate and evaporated to an oil which is purified via column chromatography on 750 g. of silica gel eluted with 50% ether-hexane to yield 33 g. (100%) of product as an oil.

IR: (CHCl$_3$) 1667, 1631, 1595 and 1563 cm$^{-1}$. UV: $\lambda_{max}^{95\% \ ethanol}$ ($\epsilon$) 271 (12,100) and 314 (5,790) nm. PMR: $\epsilon_{CDCl_2}^{TMS}$ 1.33 (d, J=6 Hz, sidechain methyl), 1.45 (s, C-2 methyls), 1.77 (m, two sidechain methylenes), 2.67 (m, benzylic sidechain methylene), 2.70 (s, C-3 methylene), 4.45 (m, sidechain methine), 6.32 (d, J=2 Hz, C-8 ArH), 6.73 (d, J=2 Hz, C-6 ArH), 6.93 (d, J=16 Hz, vinyl proton), 7.22 (s, PhH), 7.1-7.8 (m, PhH) and 0.97 (d, J=16 Hz, vinyl proton).

MS: m/e 440 (M+), 294 and 279.

Method B: to a solution of 2,2-dimethyl-7-hydroxy-5-(2-phenylethenyl)-4-chromanone (21.8 g., 74.1 mmoles) and potassium hydroxide (4.16 g., 74.2 mmoles) in N,N-dimethylformamide (58 ml.) is added with stirring 2-bromo-5-phenylpentane (17.03 g., 75 mmoles). The mixture is heated for four days at 100° C., cooled to room temperature and then added to a mixture of aqueous sodium hydroxide (100 ml. of 1 N), water (45 ml.) and chloroform (150 ml.). The mixture is agitated and the chloroform layer separated. The aqueous layer is extracted with more chloroform (150 ml.). The combined chloroform layers are washed with 1 N sodium hydroxide (2×100 ml.) dried over sodium sulfate and concentrated to an oil. The unreacted 2-bromo-5-phenylpentane is removed by distillation and the residue purified by silica gel chromatography to give the title product as an oil.

Similarly, the following compounds are prepared from the appropriate 2,2-$R_2R_3$-7-hydroxy-5-(2-phenylethenyl)-4-chromanone and the appropriate mesylate $CH_3SO_2\text{-}O\text{-}(alk_2)_n\text{-}W$ or Br-Z-W reactant.

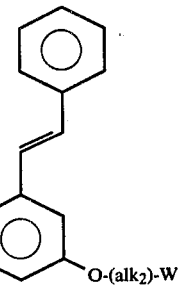

| R₂ | R₃ | (alk₂) | W | Method |
|---|---|---|---|---|
| CH₃ | CH₃ | C(CH₃)₂(CH₂)₆ | H | A |
| CH₃ | CH₃ | CH(CH₃)CH(CH₃)(CH₂)₅ | H | A |
| CH₃ | CH₃ | CH₂ | H | A |
| H | CH₃ | (CH₂)₅ | H | A |
| H | CH₃ | (CH₂)₁₀ | H | A |
| H | H | (CH₂)₅ | H | B |
| H | H | CH(CH₃)CH(CH₃)(CH₂)₅ | H | A |
| H | H | CH(CH₃)(CH₂)₃ | 4-FC₆H₄ | A |
| H | CH₃ | CH(CH₃)(CH₂)₃ | 4-ClC₆H₄ | B |
| CH₃ | CH₃ | (CH₂)₅ | C₆H₅ | B |
| H | H | CH(CH₃)CH₂ | H | A |
| H | H | CH(CH₃)(CH₂)₄ | H | A |
| H | H | CH(CH₃)(CH₂)₈ | H | A |
| H | CH₃ | CH(CH₃)CH₂ | 2-pyridyl | A |
| H | CH₃ | (CH₂)₃ | 2-pyridyl | A |
| CH₃ | CH₃ | CH(CH₃)(CH₂)₃ | 4-pyridyl | A |
| CH₃ | CH₃ | CH(CH₃)(CH₂)₈ | C₆H₅ | B |
| H | CH₃ | CH(CH₃)(CH₂)₇ | H | B |
| H | H | (CH₂)₅ | H | B |
| CH₃ | CH₃ | (CH₂)₁₀ | C₆H₅ | B |
| CH₃ | CH₃ | CH₂ | 4-FC₆H₄ | A |
| CH₃ | CH₃ | CH(CH₃)(CH₂)₈ | 3-pyridyl | A |
| H | H | C(CH₃)₂(CH₂)₃ | 3-pyridyl | A |

EXAMPLE 3

Bis-(2,2-dimethyl-7-hydroxy-5-methylidene-4-chromanone)

A mixture of 7.26 g. (0.0297 mole) of 3,3′,5,5′-tetrahydroxystilbene and 8.92 g. (0.0892 mole) of 3,3-dimethylacrylic acid in 29 ml. of borontrifluoride etherate complex is stirred at 25° C. for 39 hours. The reaction mixture is then diluted with 30 ml. of water and then 200 ml. of cold 5 N sodium hydroxide. The resultant mixture is acidified with 90 ml. of concentrated hydrochloric acid forming a light yellow precipitate. The precipitate is filtered, washed with water and air dired. The dried precipitate is slurried in ether, boiled gently, cooled and filtered to yield 7.05 g. (58%) of the title product as a light yellow solid.

PMR: $\delta_{D6\text{-}DMSO}^{TMS}$ 1.43 (s, C-2 methyls), 2.75 (s, methylene), 5.58 (d, J=2 Hz, C-8 ArH), 6.81 (d, J=2 HZ, C-6 ArH) and 8.01 (s, vinyl proton).

Similarly, the following compounds are prepared by using the appropriate acrylic acid, R₂R₃C═CH-COOH, as reactant in place of 3,3-dimethylacrylic acid.

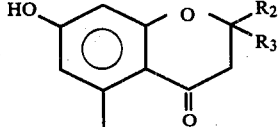

| R₂ | R₃ |
|---|---|
| H | H |
| H | CH₃ |

EXAMPLE 4

Bis-(2,2-Dimethyl-7-[2-(5-phenylpentyloxy)]-5-methylidene-4-chromanone)

A mixture of 3.00 g. (7.30 mmoles) of bis-(2,2-dimethyl-7-hydroxy-5-methylidene-4-chromanone), 4.60 g. (18.9 mmoles) of 2-(5-phenylpentyl)-methanesulfonate and 3.94 g. (28.6 mmoles) of anhydrous potassium carbonate in 25 ml. of dimethylformamide is heated at 85° C. for 16 hours. The reaction mixture is then cooled and added to 250 ml. ether-250 ml. water. The organic phase is separated and washed twice with 200 ml. of water, dried over magnesium sulfate and evaporated to an oil. Crystallization of the oil in ether gives 1.3 g. (25%) of the title product. Column chromatography of the mother liquor on 250 g. of silica gel eluted with 50% ether-petroleum ether gives another 1.01 g. (20%) of crystalline product (from ether). Crystallization of a more polar fraction from ether affords 0.42 g. (10%) of monoalkylated product (m.p. 172°–173° from ether).

Bis-(2,2-dimethyl-7-[2-(5-phenylpentyloxy)]-5-methylidene-4-chromanone):

M.P.: 109° C. (from ether)

IR: (CHCl₃) 1658, 1587 and 1570 cm⁻¹.

UV: $\lambda_{max}^{95\% \text{ ethanol}}$ ($\epsilon$) 359 (25,800), 310 (34,700) and 262 (89,700) nm.

PMR: $\delta_{CDCl_3}^{TMS}$ 1.35 (d, J=6 Hz, sidechain methyl), 1.48 (s, C-2 methyls), 1.78 (m, two methylene of sidechain), 2.72 (s, C-3-methylene), 2.72 (m, sidechain benzylic methylene), 4.53 (m, sidechain methine), 6.35 (d, J=2 Hz, C-8 ArH), 7.00 (d, J=2 Hz, C-8 ArH), 7.28 (s, PhH) and 8.10 (s, vinyl proton).

MS: m/e 700 (M+) and 408 (100%).

Analysis: Calc'd for C₄₆H₅₂O₆: C, 78.82; H, 7.48%; Found: C, 78.72; H, 7.49%.

In like manner, the compounds listed below are prepared by replacing 2-(5-phenylpentyl)-methanesulfonate with the appropriate reactant of formula CH₃SO₂—O—(alk₂)-W.

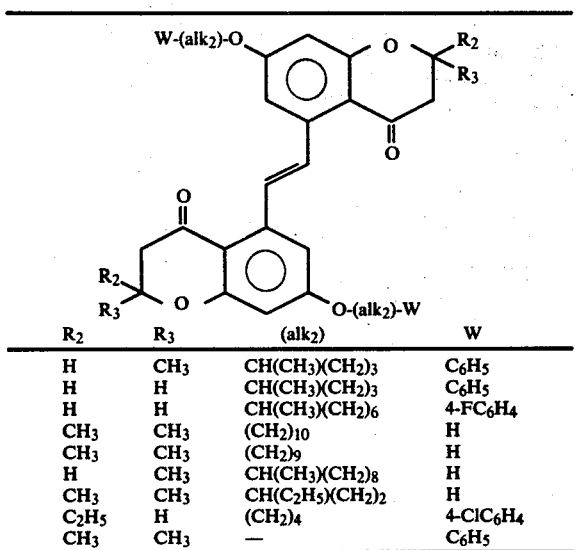

| R2 | R3 | (alk2) | W |
|---|---|---|---|
| H | CH3 | CH(CH3)(CH2)3 | C6H5 |
| H | H | CH(CH3)(CH2)3 | C6H5 |
| H | H | CH(CH3)(CH2)6 | 4-FC6H4 |
| CH3 | CH3 | (CH2)10 | H |
| CH3 | CH3 | (CH2)9 | H |
| H | CH3 | CH(CH3)(CH2)8 | H |
| CH3 | CH3 | CH(C2H5)(CH2)2 | H |
| C2H5 | H | (CH2)4 | 4-ClC6H4 |
| CH3 | CH3 | — | C6H5 |

EXAMPLE 5

2,2-Dimethyl-7-[2-(5-phenylpentyloxy)]-chroman-4-on-5-carboxaldehyde

Method A

A mixture of 30.0 g. (68.1 mmoles) of 2,2-dimethyl-5-(2-phenylethenyl)-7-[2-(5-phenylpentyloxy)]-4-chromanone, 43.8 g. (204 mmoles) of sodium periodate and 169 mg. (0.67 mmole) of osmium tetroxide in 272 ml. of dioxane and 68 ml. water is stirred at 25° C. for 15 hours. The reaction mixture is then added to a mixture of one liter of ether and 500 ml. of 15% sodium sulfite solution. The ether extract is washed with 500 ml. of saturated sodium bicarbonate and evaporated to an oil which is purified via column chromatography on 750 g. of silica gel eluted with 40% ether-petroleum ether to yield 24 g. (96%) of product as an oil.

Method B

A mixture of 1.0 g. (1.42 mmoles) of bis-(2,2-dimethyl-7-[2-(5-phenylpentyloxy)]-5-methylene-4-chromanone), 2 mg. (0.008 mmole) osmium tetroxide and 942 mg. (4.40 mmole) sodium periodate in 8 ml. dioxane and 2 ml. water is stirred at 25° C. for 24 hours. The reaction mixture is added to 200 ml. ether-150 ml. water. The organic phase is separated and washed successively with 100 ml. of 10% sodium sulfite and 100 ml. saturated sodium bicarbonate. It is then dried over magnesium sulfate and evaporated to give 1.09 g. (100%) of product as an oil.

IR: (CHCl3) 1678, 1600 and 1587 cm$^{-1}$.

UV: $\lambda_{max}^{45\% \text{ ethanol}}$ ($\epsilon$) 238 (35,000), 255 (16,800), 287 (12,200) and 336 (9,260) nm.

PMR: $\delta_{CDCl_3}^{TMS}$ 1.31 (d, J=6 Hz, sidechain methyl), 1.50 (s, C-2 methyls), 1.75 (m, two sidechain methylenes), 2.63 (m, benzylic sidechain methylene), 2.78 (s, C-3 -methylene), 4.5 (m, sidechain methine), 6.60 (d, J=2 Hz, C-8 ArH), 6.98 (d, J=2 Hz, C-6 ArH), 7.28 (s, PhH) and 10.78 (s, CHO).

MS: m/e 366 (M+), 338, 192 and 177.

Similarly, application of the above procedures to the products of Examples 3 and 4 afford compounds having the formula shown below wherein each of R2, R3, Z and W is as defined in Examples 1–4.

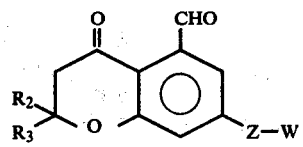

EXAMPLE 6

2,2-Dimethyl-5-hydroxymethyl-7-[2-(5-phenylpentyloxy)]-4-chromanone

To a −78° C. solution of 20.0 g. (54.6 mmoles) of 2,2-dimethyl-7-[2-(5-phenylpentyloxy)]-chroman-4-on-5-carboxaldehyde in 400 Ml. of tetrahydrofuran is added dropwise (45 minutes) 109.3 ml. (54.6 mmoles) of a 0.5 M tetrahydrofuran solution of potassium tri-sec-butylborohydride. After 30 minutes the reaction mixture is added to a mixture of one liter each of ether and saturated sodium chloride. The ether extract is washed with 500 ml. saturated sodium chloride, dried over magnesium sulfate and evaporated to an oil. This oil is purified via column chromatography on 750 g. of silica gel eluted with 50% ether-petroleum ether to yield 19.3 g. (96%) of the title product as an oil.

IR: (CHCl3) 3436, 1667, 1608 and 1587 cm$^{-1}$.

PMR: $\delta_{CDCl_3}^{TMS}$ 1.30 (d, J=6 Hz, sidechain methyl), 1.45 (s, C-2 methyl), 1.73 (m, two sidechain methylenes), 2.66 (m, benzylic sidechain methylene), 2.71 (s, C-3 methylene), 4.46 (m, sidechain methine), 4.68 (bs, hydroxymethylene), 6.31 (d, J=2 Hz, C-8 ArH), b 6.51 (d, J=2 Hz, C-6 ArH) and 7.25 (s, PhH).

MS: m/e 368 (M+$^L$), 353, 340 and 222.

In like manner the remaining compounds of Example 5 are reduced to the corresponding 5-hydroxymethyl derivatives of the formula:

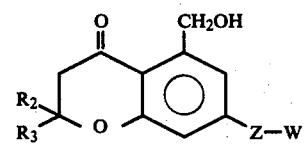

wherein R2, R3, Z and W have the values given in Example 5.

EXAMPLE 7

2,2-Dimethyl-5-hydroxymethyl-3-(3-oxobutyl)-7-[2-(5-phenylpentyloxy)]-4-chromanone A solution of 16.0 g. (43.4 mmoles) of 2,2-dimethyl-5-hydroxymethyl-7-[2-(5-phenylpentyloxy)]-4-chromanone in 50 ml. of ethyl formate and 40 ml. ether is added, over a 15 minute period, to 5.2 g. (0.217 mole) of sodium hydride in a 10° C. bath. After stirring one hour at 15° C. the reaction mixture is added to a mixture of 500 ml. ethyl acetate-300 ml. saturated sodium chloride-25 ml. concentrated hydrochloric acid. The organic extract is separated, dried over magnesium sulfate and evaporated to an oil [2,2-dimethyl-3-hydroxymethylene-5-hydroxymethyl-7-[2-(5-phenylpentyloxy)]-4-chromanone]. This crude product is dissolved in 130 ml. methanol-10 ml. ether and 6.07 ml. (43.4 mmoles) of triethylamine and 10.5 ml. (0.130 mmole) of methyl vinyl ketone added. The reaction mixture is stirred for 18 hours at 25° C. to give the intermediate 2,2-dimethyl-5-hydroxymethyl-3-formyl-3-(3-oxobutyl)-7-[2-(5-phenylpentyloxy)]-4-chromanone. The mixture is then cooled to 0° C. followed by addition of 30 ml. of 2 N potassium hydroxide in methanol. The reaction mixture is stirred for 15 minutes at 0° C. and is then evaporated under reduced pressure to a thick oil (t<25° C.). The residue is dissolved in 200 ml. water-500 ml. ether. The ether extract is separated and washed once each with 200 ml. concentrated potassium carbonate and 200 ml. saturated sodium chloride. The extract is dried over magnesium sulfate and evaporated to an oil. This oil is purified via column chromatography on 700 g. silica gel eluted with ether to yield 6.5 g. (34%) of the title product as an oil.

IR: (CHCl$_3$) 3401, 1718, 1656, 1603 and 1575$^{-1}$.

PMR: $\delta_{CDCl_3}{}^{TMS}$ 1.33 (d, J=6 Hz, sidechain CH$_3$), 1.43, 1.48 (s, C-6 CH$_3$) 2.18 (s, CH$_3$CO), 4.65 (s, CH$_2$OH), 4.6 (m, OH, sidechain methine), 6.33 (d, J=2 Hz, ArH), 6.55 (d, J=2 Hz, ArH), 6.55 (d, J=2 Hz, ArH), and 7.30 (s, PhH).

MS: m/e 438 (M+), 423, 420, 277 and 274.

The total aqueous extract is cooled to 0° C. and acidified with concentrated hydrochloric acid. Extraction with ether followed by drying of the ether extract over magnesium sulfate and evaporation gives a second residue (5.4 g.). Column chromatography of this residue on silica gel eluted with 50% ether-CH$_2$Cl$_2$ yields 7-hydroxy-5-[2-(5-phenylpentyloxy)]-phthalide as a solid.

7-Hydroxy-5-[2-(5-phenylpentyloxy)]-phthalide:
IR: (CHCl$_3$) 3425, 1733 and 1626 cm$^{-1}$.

PMR: $\delta_{CDCl_3}{}^{TMS}$ 1.35 (d, J-6 Hz, sidechain CH$_3$), 1.80 (m, sidechain CH$_2$CH$_2$) 2.70 (m, CH$_2$Ph), 4.50 (m, sidechain methine), 5.30 (s, OCH$_2$Ar), 6.50 (s, ArH), and 7.32 (s, PhH).

MS: m/e 312 (M+), 167 and 166.

Similarly, the remaining products of Example 6 are converted to compounds of the formula

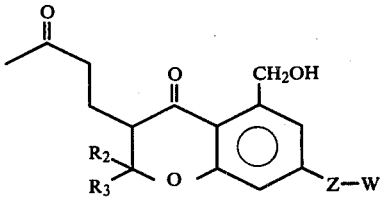

wherein the variables R$_2$, R$_3$, Z and W are as defined in Example 6.

The corresponding phthalides having the formula shown below are produced as by-product in each instance.

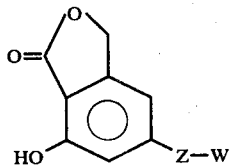

EXAMPLE 8

6a,7-Dihydro-6,6-dimethyl-1-hydroxymethyl-3-[2-(5-phenylpentyloxy)]-6H-dibenzo[b,d]pyran-9(8H)-one A solution of 6.0 g. (13.7 mmoles) of 2,2-dimethyl-5-hydroxymethyl-3-(3-oxobutyl)-7-[2-(5-phenylpentyloxy)]-4-chromanone in 400 ml. of 1 N potassium hydroxide in methanol is heated 3.5 hours at reflux and then stirred for 15 hours at 25° C. The reaction mixture is evaporated to a small volume under reduced pressure (t<25° C.) and diluted with 500 ml. of ether, 500 ml. water and 65 ml. concentrated hydrochloric acid. The ether extract is separated, washed twice with 300 ml. portions of saturated sodium chloride, dried over magnesium sulfate and evaporated to an oil. The crude oil is purified via column chromatography on 500 g,. of silica gel eluted with 2:1 ethyl acetate: cyclohexane to yield 2.0 g. (35%) of 6a,7-dihydro-6,6-dimethyl-1-hydroxymethyl-3-[2-(5-phenylpentyloxy)]-6H-dibenzo[b,d]pyran-9(8H)-one and 1.0 g. (17.5%) of 3-hydroxymethyl-2-[3-(4-isopropylidenylcyclohexenone)]-5-[2-(5-phenylpentyloxy)]phenol as a solid.

6a,7-Dihydro-6,6-dimethyl-1-hydroxymethyl-3-[2-(5-phenylpentyloxy)]6H-dibenzo[b,d]pyran-9(8H)-one:

Oil; IR: (CHCl$_3$) 3571, 3390, 1656, 1613 and 1587 cm$^{-1}$.

PMR: $\delta_{CDCl_3}{}^{TMS}$ 1.20 (s, C-6 CH$_3$), 1.32 (d, J=6 Hz, sidechain CH$_3$), 1.53 (s, C-6 CH$_3$), 4.4 (m, sidechain methine), 4.82 (s, CH$_2$OH), 6.40 (d, J=3 Hz, ArH), 6.58 (d, J=2 Hz, C-10 vinyl proton), 6.85 (d, J=3 Hz, ArH) and 7.32 (s, PhH).

uv: $\lambda_{max}{}^{95\% \ EtOH}$ ($\epsilon$) 350 (34,500), 313 (23,200), 253 (15,800) and 228 (18,000).

MS: m/e 420 (M+), 405, 274, 259 and 256.

3-Hydroxymethyl-2-[3-(4-isopropylidenecyclohexenone)]-5-[2-(5-phenylpentyloxy)]-phenol:

M.P. 125°-128° C.

IR: (CHCl$_3$) 3484, 3125, 1667, 1647, 1613 and 1597 cm$^{-1}$.

PMR: $\delta_{CDCl_3}{}^{TMS}$ 1.30 (d, J=6 Hz, sidechain CH$_3$), 1.33, 1.48 (s, C-6 CH$_3$), 1.5-3.0 (m), 4.35 (m, sidechain methine), 4.50, 4.90 (AB, J=16 Hz, CH$_2$OH), 6.25 (d, J=2 Hz, ArH), 6.48 (d, J=2 Hz, ArH), 6.98 (s, vinyl proton), 7.23 (s, PhH), and 7.9 (bs, OH).

MS: m/e 420 (M+), 405, 274 and 259.

EXAMPLE 9 dl-6a$\beta$,7,10,10a$\beta$-Tetrahydro-6,6-dimethyl-1-hydroxymethyl-3-[2-(5-phenylpentyloxy)]-6H-dibenzo[b,d]pyran-9(8H)-one and the 6a$\beta$,10a$\beta$-Isomer To a −78° C. solution of 88 mg. (12.6 mmoles) of lithium metal in 200 ml. of liquid ammonia and 75 ml. of tetrahydrofuran is added a solution of 2.0 g. (4.76 mmoles) of 6a,7-dihydro-6,6-dimethyl-1-hydroxymethyl-3-[2-(5-phenylpentyloxy)]-6H-dibenzo[b,d]pyran-9(8H)-one in 75 ml. of tetrahydrofuran. An additional 44 mg. (6.3 mmoles) and 11 mg. (1.6 mmoles) of lithium is added to keep the reaction blue during addition of the enone. After the addition is complete (5 minutes), the reaction mixture is stirred for 15 minutes and then quenched with excess solid ammonium chloride. The ammonia is allowed to evaporate and the residue added to 250 ml. ether-50 ml. saturated ammonium chloride. The organic phase is separated, dried over magnesium sulfate and evaporated to an oil. This oil is purified via column chromatography on 200 g. of silica gel eluted in 10 ml. fractions with ether to yield 1.21 g. (61%) of dl-6a$\beta$,7,10,10a$\beta$-tetrahydro-6,6-dimethyl-1-hydroxymethyl-3-[2-(5-phenylpentyloxy)]-6H-dibenzo[b,d]pyran-](8H)-one and 0.29 g. (15%) of the 6a$\beta$,10a$\beta$-isomer.

dl-6a$\beta$,7,10,10a$\alpha$-tetrahydro-6,6-dimethyl-1-hydroxymethyl-3-[2-(5-phenylpentyloxy)]-6H-dibenzo[b,d]pyran-9(8H)-one:

IR: (CHCl$_3$) 3571, 3390, 1718, 1618 and 1582 cm$^{-1}$.

PMR: $\delta_{CDCl_3}^{TMS}$ 1.12 (s, C-6 methyl), 1.28 (d, J=6 Hz, sidechain methyl), 1.50 (s, C-6 methyl), 4.40 (m, sidechain methine), 4.68 (s, hydroxymethylene), 6.35 (d, J=2 Hz, C-4 ArH), 6.61 (d, J=2 Hz, C-2 ArH), and 7.26 (s, PhH).

MS: m/e 422 (M+), 408, 394, 276, 261 and 258.

dl-6aβ,7,10,10aβ-tetrahydro-6,6-dimethyl-1-hydroxymethyl-3-[2-(5-phenylpentyloxy)]-6H-dibenzo[b,d]pyran-9(8H)-one:

IR: (CHCl$_3$) 3546, 3390, 1715, 1613 and 1580 cm$^{-1}$.

PMR: $\delta_{CDCl_3}^{TMS}$ 1.28 (d, J=6 Hz, sidechain methyl), 1.33 and 1.38 (s, C-6 methyls), 4.30 (m, sidechain methine), 4.67 (bs, hydroxymethylene), 6.38 (d, J=2 Hz, C-4 ArH), 6.63 (d, J=2 Hz, C-2 ArH) and 7.23 (s, PhH).

MS: m/e 422 (M+), 407, 276 and 261.

Following the procedure of Example 8 and that given above, the remaining compounds of Example 7 are converted to the isomeric compounds having the formula

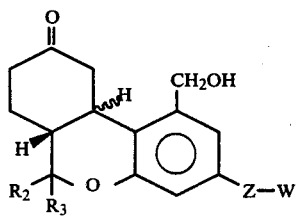

wherein R$_2$, R$_3$, Z and W are as defined in Example 7 and the wavy line at the 10a-position indicates the α- and β-forms.

EXAMPLE 10

6aβ,7,8,9,10,10aα-Hexahydro-6,6-dimethyl-1-hydroxymethyl-3-[2-(5-phenylpentyloxy)]-6H-dibenzo[b,d]pyran-9β-ol To a −78° C. solution of 50 mg. (0.118 mmole) of 6aβ,7,10,10aα-tetrahydro-6,6-dimethyl-1-hydroxymethyl-3-[2-(5-phenylpentyloxy)]-6H-dibenzo[b,d]pyran-9(8H)-one in 1 ml. of methanol is added 10 mg. (0.26 mmole) of sodium borohydride. The reaction mixture is stirred for 40 minutes and is then added to 100 ml. ether-100 ml. saturated sodium chloride solution. The organic extract is separated, dried over magnesium sulfate and evaporated to give a quantitative yield of the title product as an oil.

PMR: $\delta_{CDCl_3}^{TMS}$ 1.05 (s, C-6 methyl), 1.28 (d, J=6 Hz, sidechain methyl), 1.40 (s, C-6 methyl), 4.40 (m, sidechain methine), 4.70 (s, C-1' methylene), 6.30 (d, J=2 Hz, C-4 ArH), 6.58 (d, J=2 Hz, C-2 ArH) and 7.23 (s, PhH).

Reduction of the 6aβ,10aα-isomeric compounds of Example 9 in like manner affords compounds of the formula below wherein the variables R$_2$, R$_3$, Z and W are as defined in Example 9.

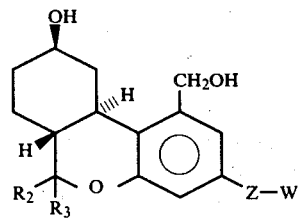

EXAMPLE 11

6aβ,7,8,9,10,10aβ-Hexahydro-6,6-dimethyl-1-hydroxymethyl-3[2-(5-phenylpentyloxy)]-6H-dibenzo[b,d]pyran-9β-ol To a −15° C. solution of 70 mg. (0.166 mmole) of 6aβ,7,10,10aβ-tetrahydro-6,6-dimethyl-1-hydroxymethyl-3-[2-(5-phenylpentyloxy)]-6H-dibenzo[b,d]pyran-9(8H)-one in 1 ml. of methanol is added 15 mg. (0.395 mmole) of sodium borohydride. The reaction mixture is stirred for 20 minutes and is then added to 50 ml. saturated sodium chloride solution and 150 ml. ether. The ether extract is separated, dried over magnesium sulfate and evaporated to an oil. The oil is purified via preparative layer chromatography on two 20 cm×20 cm×0.5 mm silica gel plates eluted with 5% methanol-ether to yield 68 mg. (97%) of the title product as an oil.

PMR: $\delta_{CDCl_3}^{TMS}$ 1.28 (d, J=6 Hz, sidechain methyl), 1.35 (s, C-6 methyl), 1.45 (s, C-6 methyl), 3.90 (m, C-9 methine), 4.40 (m, sidechain methine), 4.68 (s, C-1' methylene), 6.38 (d, J=2 Hz), C-4 ArH), 6.62 (d, J=2 Hz, C-2ArH) and 7.30 (s, PhH).

IR: (CHCl$_3$) 3571, 3390, 1616 and 1582 cm$^{-1}$.

MS: m/e 424 (M+), 278, 263, 260 and 245.

The remaining 6aβ,10aβ-isomeric compounds of Example 9 are reduced in like manner to give compounds having the formula

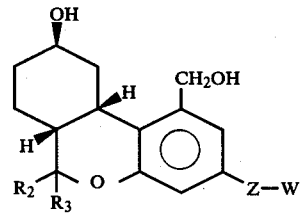

wherein R$_2$, R$_3$, Z and W are as defined in Example 9.

EXAMPLE 12 dl-6aβ,7,10,10aα-Tetrahydro-1-hydroxymethyl-3-[2-(5-phenylpentyloxy)]-6,6-dimethyl-6H-dibenzo[b,d]pyran-9(8H)-one ethylene ketal A mixture of 500 mg. (1.18 mmoles) of dl-6aβ,7,10,-10aα-tetrahydro-1-hydroxymethyl-3-[2-(5-phenylpentyloxy)]-6,6-dimethyl-6H-dibenzo[b,d]pyran-9(8H)-one, 1 ml. (17.8 mmoles) of ethylene glycol, 20 ml. of benzene and several crystals of p-toluenesulfonic acid monohydrate is heated at reflux with a Dean Stark trap for one hour. The reaction mixture is cooled and added to 150 ml. ether-100 ml. saturated sodium bicarbonate. The organic phase is separated, washed once with 100 ml. water, dried over magnesium sulfate and evaporated under reduced pressure to give a quantitative yield of the title ketal as an oil, R$_f$=0.43 (silica gel, 0.25 mm, eluted with ether).

Repetition of this procedure, but substituting propylene glycol or butylene glycol for ethylene glycol affords the corresponding ketals.

EXAMPLE 13 dl-6aβ,7,10,10aα-Tetrahydro-3-[2-(5-phenylpentyloxy)]-9,9-ethylenedioxy-6,6-dimethyl-6H-dibenzo[b,d]pyran-1-carboxaldehyde To a 0° C. solution of 550 mg. (1.18 mmoles) of dl-6aβ,7,10,10aα-tetrahydro-1-hydroxymethyl-3-[2-(5-phenylpentyloxy)]-6,6-dimethyl-6H-dibenzo[b,d]pyran-9(8H)-one ethylene ketal in 10 ml. of dichloromethane is added 492 mg. (6.0 mmoles) of sodium acetate and 254 mg. (1.18 mmoles) of pyridinium chlorochromate. After 30 minutes of stirring, another 254 mg. (1.18 mmoles) of pyridinium chlorochromate is added followed, after an additional 30 minutes, by 1 g. of solid sodium bicarbonate and 30 ml. of ether. The reaction mixture is filtered through several grams of silica gel and the filtrate evaporated to give a quantitative yield of the title product as an oil, $R_f = 0.72$ (silica gel, 0.25 mm, eluted with ether).

EXAMPLE 14 dl-6aβ,10,10aα-Tetrahydro-3-[2-(5-phenylpentyloxy)]-6,6-dimethyl-6H-dibenzo[b,d]pyran-1-carboxylic acid-9(8H)-one ethylene ketal To a refluxing solution of 548 mg. (1.18 mmoles) of dl-6aβ,7,10,10aα-tetrahydro-3-[2-(5-phenylpentyloxy)]-9,9-ethylenedioxy-6,6-dimethyl-6H-dibenzo[b,d]pyran-1-carboxaldehyde in 10 ml. of acetone is added slowly 3.36 ml. of a 0.5 M potassium permanganate solution. The reaction mixture is refluxed 30 minutes longer and is then filtered through supercel. The filtrate is evaporated and the residue dissolved in 200 ml. ether-50 ml. saturated sodium chloride-2 ml. 1 N hydrochloric acid. The organic phase is separated, dried over magnesium sulfate and evaporated to an oil, $R_f = 0.42$ (0.25 mm silica gel, eluted with 1:1 ether:ethyl acetate). Yield = quantitative.

EXAMPLE 15 dl-6aβ,7,10,10aα-Tetrahydro-3-[2-(5-phenylpentyloxy)]-6,6-dimethyl-6H-dibenzo[b,d]pyran-1-carboxamide-9(8H)-one ethylene ketal To a solution of 566 mg. (1.18 mmoles) of dl-6aβ,7,10,10aα-tetrahydro-3-[2-(5-phenylpentyloxy)]-6,6-dimethyl-6H-dibenzo[b,d]pyran-1-carboxylic acid-9(8H)-one ethylene ketal in 2 ml. of ether is added 1.18 ml. of 2 N sodium hydroxide solution. The aqueous phase is separated, washed several times with ether, evaporated under vacuum to a solid which is dried by heating for 3 hours at 110° C., 0.2 torr. The solid is then slurried in 5 ml. of toluene cooled to 0° C. and 2.36 mmoles of oxalyl chloride added. The reaction mixture is stirred for 3 hours at 0° C., 16 hours at 25° C., and then cooled to −10° C. Anhydrous ammonia is bubbled through the reaction for several minutes, forming a thick precipitate. The reaction mixture is warmed to 25° C. and added to 150 ml. of 1:1 ether:ethyl acetate and 100 ml. of 0.5 N sodium hydroxide. The organic phase is separated, dried over magnesium sulfate and evaporated to yield the title product (187 mg., 33%, powder from pentane).

IR- (CHCl$_3$) 3497, 3378, 1684, 1613 and 1580 cm$^{-1}$.
PMR: $\delta_{CDCl_3}^{TMS}$ 1.15 (s, C-6 methyl), 1.27 (d, J=6 Hz, sidechain methyl), 1.42 (s, C-6 methyl), 4.10 (bs, −OCH$_2$CH$_2$O−), 4.1 (m, sidechain methine), 6.1 (bm, NH$_2$), 6.42 (d, J=2 Hz, ArH), 6.60 (d, J=2 Hz, ArH) and 7.27 (s, PhH). MS: m/e 479 (M$^+$)

EXAMPLE 16 dl-6aβ,7,10,10aα-Tetrahydro-1-amino-6,6-dimethyl-3-[2-(5-phenylpentyloxy)]-6H-dibenzo[b,d]pyran-9(8H)-one To a 0° C. solution of 130 mg. (0.271 mmole) of dl-6aβ,7,10,10aα-tetrahydro-3-[2-(5-phenylpentyloxy)]-6,6-dimethyol-6H-dibenzo[b,d]pyran-2-carboxamide-9(8H)-one ethylene ketal in 1 ml. of dioxane is added 0.6 ml. of a 0.5 M solution of sodium hypobromite. After stirring for 15 minutes at 0° C., the reaction mixture is heated at 100° C. for 10 minutes. It is then cooled and added to 100 ml. of saturated sodium bicarbonate and 150 ml. ether. The ether extract is separated, dried over magnesium sulfate and evaporated to an oil. This oil is dissolved in 2 ml. of tetrahydrofuran and 2 ml. of 1 N hydrochloric acid. The mixture is stirred at 25° C. for one hour, refluxed for 30 minutes and stirred at 25° C. an additional 12 hours. The reaction mixture is then added to 150 ml. ether-50 ml. saturated sodium bicarbonate. The ether extract is separated, dried over magnesium sulfate and evaporated to an oil which is purified via preparative thin layer chromatography on three 20 cm.×20 cm.×0.5 mm silica gel plates eluted with 80% ether-pentane to yield 33 mg. (30%) of the title product as an oil.

PMR: $\delta_{CDCl_3}^{TMS}$ 1.13 (s, C-6 methyl), 1.27 (d, J=6 Hz, sidechain methyl), 1.48 (s, C-6 methyl), 3.5 (bm, NH$_2$), 4.2 (m, sidechain methine), 5.80 and 5.90 (d, J=3 Hz, ArH) and 7.20 (s, PhH).

Similarly, the compounds of Example 9 are converted via the procedures of Examples 12–15 and the above procedure to compounds having the following formula wherein R$_2$, R$_3$, (alk$_2$) and W are as defined in Example 9, and the wavy line at the 10a-position represents the α- and β-forms:

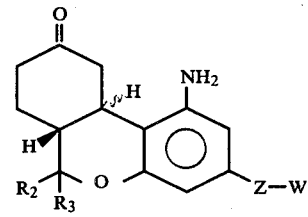

EXAMPLE 17 dl-6aβ,7,8,9,10,10aα-Hexahydro-1-amino-6,6-dimethyl-3-[2-(5-phenylpentyloxy)]-6-H-dibenzo[b,d]pyran-9β-ol To a −78° C. solution of 27 mg. (0.0663 mmole) of dl-6aβ,7,10,10aα-tetrahydro-1-amino-6,6-dimethyl-3-[2-(5-phenylpentyloxy)]-6H-dibenzo[b,d]pyran-9(8H)-one in 2 ml. ethanol and 0.5 ml. ether is added 15 mg. (0.4 mmole) of sodium borohydride. The reaction mixture is stirred for 30 minutes at −78° C. and for 10 minutes at 0° C. followed by quenching with 1 N hydrochloric acid and addition to 150 ml. ether and 50 ml. saturated sodium bicarbonate. The ether extract is dried over magnesium sulfate and evaporated to an oil. The crude oil is purified via preparative thin layer chromatography on a 20 cm×20 cm×0.5 mm silica gel plate eluted with 80% ether-pentane to yield 5.0 mg. (19%) of the desired product.

MS: m/e 409.2617 (M+, Calc'd for $C_{26}H_{35}NO_3$=409.2718), 394, 351, 318, 304, 290, 263, 248, 230 and 205.

The remaining products of Example 16 are reduced in like manner to give compounds having the formula

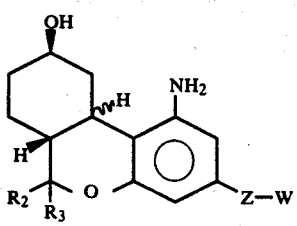

EXAMPLE 18 dl-6aβ,8,10,10aα-Tetrahydro-1-hydroxy-6,6-dimethyl-3-[2-(5-phenylpentyloxy)]-6H-dibenzo[b,d]pyran-9(8H)-one Ethylene Ketal A mixture of 6.6 g. (16.1 mmoles) of dl-6aβ,7,10,-10aα-tetrahydro-1-hydroxy-6,6-dimethyl-3-[2-(5-phenylpentyloxy)]-6H-dibenzo[b,d]pyran-9(8H)-one, 8.99 ml. (0.161 mole) of ethylene glycol and 500 mg. of p-toluenesulfonic acid monohydrate in 100 ml. of benzene is heated under reflux with a Dean-Stark trap for 1 hour. The reaction mixture is cooled and added to 100 ml. ether and 100 ml. saturated sodium bicarbonate. The organic phase is separated, washed once with 100 ml. of saturated sodium bicarbonate, dried over magnesium sulfate and evaporated to yield 7.26 g. (100%) of the ethylene ketal as an oil.

IR: (CHCl₃) 3571, 3300, 1623 and 1587 cm$^{-1}$.

PMR: $\delta_{CDCl_3}{}^{TMS}$ 1.03 (s, C-6 methyl), 1.24 (d, J=6 Hz, sidechain methyl), 1.35 (s, C-6 methyl), 4.00 (s, ethylene ketal), 5.52 (s, OH), 5.78 and 5.90 (d, J=2 Hz, C-2 and C-4 ArH) and 7.18 (s, PhH).

MS: 452 (M+), 437, 407, 391 and 306.

EXAMPLE 19 dl-6aβ,7,10,10aα-Tetrahydro-1-O-diethylphosphoryl-3-[2-(5-phenylpentyloxy)]-6,6-dimethyl-6H-dibenzo[b,d]-pyran-9(8H)-one Ethylene Ketal To a 0° C. solution of 3.0 g. (6.64 mmoles) of dl-6aβ,7,10,10aα-tetrahydro-1-hydroxy-3-[2-(5-phenylpentyloxy)]-6,6-dimethyl-6H-dibenzo[b,d]pyran-9(8H)-one ethylene ketal in 12 ml. of toluene is added over a 3 minute period 1.32 ml. (6.64 mmoles) of 20% sodium hydroxide and 1.15 g. (6.64 mmoles) of diethyl chlorophosphate. After stirring for 15–30 minutes, the above portions of reagents are again added to the reaction mixture and the addition procedure repeated twice more after that. The reaction mixture is then added to 150 ml. ether - 150 ml. 10% sodium hydroxide, the organic phase separated and washed once each with 150 ml. of water and 150 ml. saturated sodium chloride. The organic extract is dried over magnesium sulfate and evaporated to yield 3.9 g. (100%) of the desired product as an oil.

IR: (CHCl₃) 1626, 1580, 1269, 1142, 1095 and 1015 cm$^{-1}$.

PMR: $\delta_{CDCl_3}{}^{TMS}$ 1.0–2.1 (m), 2.3–3.4 (m), 4.02 (m, ethylene ketal), 3.9–4.6

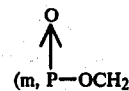

(m, P—OCH₂ and sidechain methine), 6.20 (d, J=2 Hz, C-4 ArH), 6.52 (dd, J$_H$=2 Hz, J$_P$=1 Hz, C-2 ArH) and 7.21 (s, PhH).

MS: m/e 588 (M+).

EXAMPLE 20 dl-6aβ-7,10,10aα-Tetrahydro-1-amino-3-[2-(5-phenylpentyloxy)]-6,6-dimethyl-6H-dibenzo[b,d]pyran-9(8H)-one ethylene ketal To a −78° C. mixture of 25 mmoles of potassium amide (from 975 mg. potassium, 25 mmoles, and 50 mg. of ferric nitrate nonahydrate in 50 ml. of liquid ammonia at −33° C.) in 50 ml. of liquid ammonia is simultaneously added a solution of 2.9 g. (4.93 mmoles) of dl-6aβ-7,10,10aα-tetrahydro-1-O-diethylphosphoryl-3-[2-(5-phenylpentyloxy)]-6,6-dimethyl-6H-dibenzo[b,d]-pyran-9(8H)-one ethylene ketal in 10 ml. of tetrahydrofuran and a total of 200 mg. of potassium (5.12 mmoles) in three portions. The resultant blue solution is stirred 10 minutes longer and quenched with excess ammonium chloride. The reaction mixture is allowed to warm, ether added, and the ammonia allowed to evaporate. The residue is added to 200 ml. ether and 100 ml. water, the organic phase separated, washed once with 100 ml. of saturated sodium bicarbonate, dried (magnesium sulfate) and evaporated to an oil. This oil is purified via column chromatography on 200 g. of silica gel eluted with 2:1 ether:cyclohexane to yield the following fractions in order of elution:

Fraction 1: 756 mg. (35%) of dl-6aβ-7,10,10aα-tetrahydro-3-[2-(5-phenylpentyloxy)]-6,6-dimethyl-6H-dibenzo[b,d]pyran-9(8H)-one ethylene ketal as an oil.

IR: (CHCl₃) 1623 and 1585 cm$^{-1}$.

PMR: $\delta_{CDCl_3}{}^{TMS}$ 1.18 (s, C-6 methyl), 1.28 (d, J=6 Hz, sidechain methyl), 1.43 (s, C-6 methyl), 4.03 (s, ethylene ketal), 4.33 (m, sidechain methine), 6.33 (s overlapping 6.42, C-4 ArH), 6.42 (d,d,J=8 and 2 Hz C-2 ArH), 7.03 (d, J=8 Hz, C-1 ArH) and 7.23 (s, PhH).

MS: m/e 436 (M⊕) and 290.

Fraction 2: 116 mg. (5%) of dl-6aβ-7,10,10aα-tetrahydro-1-hydroxy-3-[2-(5-phenylpentyloxy)]-6,6-dimethyl-6H-dibenzo[b,d]pyran-9(8H)-one ethylene ketal as an oil.

Fraction 3: 52 mg. (2%) mixture of Fraction 1 and 2.

Fraction 4: 848 mg. (29%) of dl-6aβ-7,10,10aα-tetrahydro-1-hydroxy-2-diethylphosphono-3-[2-(5-phenylpentyloxy)]-6,6-dimethyl-6H-dibenzo[b,d]pyran-9(8H)-one ethylene ketal as an oil.

IR: (CHCl₃) 1626, 1587, 1149, 1127, 1105, 1020 and 976 cm$^{-1}$.

PMR: $\delta_{CDCl_3}{}^{TMS}$ 1.12 (s, C-6 methyl), 1.40 (s, C-6 methyl), 4.02 (s, ethylene ketal), 5.82 (d, J$_{H-P}$=6 Hz, C-4 ArH), 7.23 (s, PhH) and 13.73 (d, J$_{H-P}$=1 Hz, phenol).

MS: m/e 588.2965 (M⊕, Calc'd 588.2852), 442, 441 and 397.

Fraction 5: 104 mg. (5%) of dl-6aβ-7,10,10aα-tetrahydro-1-amino-3-[2-(5-phenylpentyloxy)]-6,6-dimethyl-6H-dibenzo[b,d]pyran-9(8H)-one ethylene ketal as an oil.

IR: (CHCl₃) 3425, 1626 and 1587 cm$^{-1}$.

PMR: $\delta_{CDCl_3}{}^{TMS}$ 1.08 (s, C-6 methyl), 1.25 (d, J=6 Hz, sidechain methyl), 1.40 (s, C-6 methyl), 4.03 (s, ethylene ketal), 4.20 (m, sidechain methine), 5.85 and 5.92 (d, J=2 Hz, C-2 and C-4 ArH) and 7.27 (s, PhH).

MS: m/e 451 (M⊕), 436 and 305.

Similarly, the following compounds are prepared via the procedures of Examples 18 and 19 and that described above. [Starting materials are described by Fahrenholtz in U.S. Pat. No. 3,636,058; Archer, U.S. Pat. No. 3,968,125 and Netherlands specification 7612174.

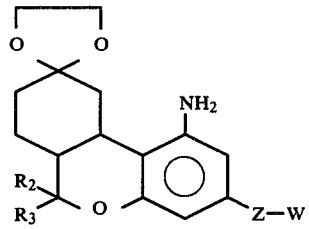

| R2 | R3 | Z | W | 6a,10a |
|---|---|---|---|---|
| CH3 | CH3 | OCH(CH3)(CH2)5 | H | cis, trans |
| CH3 | CH3 | OCH(CH3)(CH2)2 | C6H5 | trans |
| H | CH3 | OCH(CH3)(CH2)3 | C6H5 | cis, trans |
| CH3 | CH3 | O | C6H5 | trans |
| CH3 | CH3 | CH(CH3)(CH2)2O | C6H5 | trans |
| CH3 | CH3 | CH(CH3)(CH2)3 | C6H5 | cis, trans |
| CH3 | CH3 | CH(CH3)(CH2)4 | C6H5 | cis, trans |
| CH3 | CH3 | CH2CH2 | C6H5 | trans |
| CH3 | CH3 | CH(CH3)(CH2)2 | C6H5 | cis, trans |
| CH3 | CH3 | CH(CH3(CH2)3O | C6H5 | trans |
| CH3 | CH3 | CH(CH3)(CH2)3 | 4-pyridyl | trans |
| H | CH3 | CH(CH3)(CH2)3 | C6H5 | trans |
| CH3 | CH3 | CH(CH3)CH2—O—(CH2)2 | C6H5 | cis, trans |
| CH3 | CH3 | C(CH3)2(CH2)6 | H | cis, trans |
| CH3 | CH3 | (CH2)7 | H | trans |
| CH3 | CH3 | C(CH3)2(CH2)5 | H | trans |
| CH3 | CH3 | CH(CH3)CH(CH3)(CH2)5 | H | trans |
| CH3 | CH3 | C(CH3)2(CH2)2 | H | trans |
| CH3 | CH3 | (CH2)5 | H | trans |
| H | H | (CH2)7 | C6H5 | trans |
| H | H | (CH2)3 | 4-pyridyl | cis, trans |
| CH3 | H | (CH2)4 | 2-pyridyl | cis, trans |
| H | H | CH(CH3)(CH2)2 | 4-FC6H4 | cis, trans |
| CH3 | H | CH(CH3)(CH2)2 | 4-ClC6H4 | cis, trans |
| H | H | CH(CH3)(CH2)3 | 4-FC6H4 | trans |
| CH3 | CH3 | (CH2)3—O— | 4-FC6H4 | trans |
| CH3 | CH3 | CH(CH3)(CH2)2—O—(CH2)2 | C6H5 | cis, trans |
| H | H | (CH2)4—O—(CH2)5 | 4-pyridyl | trans |
| H | CH3 | (CH2)3—O—(CH2)3 | H | cis, trans |
| CH3 | CH3 | CH(C2H5)(CH2)2—O—(CH2)2 | C6H5 | trans |
| H | H | C(CH3)2(CH2)6 | H | trans |
| H | CH3 | C(CH3)2CH2 | 4-FC6H4 | cis, trans |
| H | H | C(CH3)(CH2)8 | H | trans |
| CH3 | CH3 | C(CH3)(CH2)4 | 4-ClC6H4 | trans |
| CH3 | H | C(CH3)(CH2)7 | 3-pyridyl | trans |

In each instance, the corresponding compound wherein the 1-amino group is replaced by hydrogen and by hydroxy is also produced.

EXAMPLE 21

6aβ,7,10,10aα-Tetrahydro-6,6-dimethyl-3-[2-(5-phenylpentyloxy)]-1-(O-trifluoromethylsulfonyl)-6H-dibenzo[b,d]pyran9(8H)-one Ethylene Ketal A mixture of 1.0 g. (2.21 mmoles) of 6aβ,7,10,10aα-tetrahydro-6,6-dimethyl-1-hydroxy-3-[2-(5-phenylpentyloxy)]-6H-dibenzo[b,d]pyran-9(8H)-one ethylene ketal and 0.441 g. (2.56 mmoles) of trifluoromethanesulfonyl imidazole is heated to 80° C. After the mixture becomes fluid 3 mg. of 50% sodium hydride in mineral oil is added. Additional 44 mg. (0.25 mmole) portions of trifluoromethanesulfonyl imidazole are added 70 and 85 minutes after the first addition. After 2 hours the reaction mixture is cooled and diluted with 50 ml. of ether. The resulting mixture is poured into 250 ml. water - 150 ml. ether and the ether extract washed once with 100 ml. of saturated sodium bicarbonate solution, once with 100 ml. of saturated sodium chloride solution, dried over magnesium sulfate and evaporated to yield 1.20 g. (93%) of 6aβ,7,10,10aα-tetrahydro-6,6-dimethyl-3-[2-(5-phenylpentyloxy)]-1-O-trifluoromethylsulfonyl-6H-dibenzo[b,d]pyran-9(8H)-one ethylene ketal as an oil.

PMR: $\delta_{CDCl_3}{}^{TMS}$ 1.20 and 1.23 (d, J=6 Hz, sidechain methyls), 1.10, 1.40 (s, gem dimethyl), 3.96 (bs, ethylene ketal), 4.23 (m, sidechain methine), 6.30 (s, two ArH) and 7.10 (s, Ph).

IR: (CHCl3) 1634 and 1577 cm$^{-1}$.

EXAMPLE 22

6aβ,7,10,10aα-Tetrahydro-1-amino-6,6-dimethyl-3-[2-(5-phenylpentyloxy)]-6H-dibenzo[b,d]pyran-9(8H)-one Ethylene Ketal To a −33° C. solution of 3.30 g. (60 mmole) of potassium amide (from 2.34 g., 60 mmole, of potassium and 65 mg. of ferric nitrate nonahydrate in 25 ml. of ammonia) in 25 ml. of ammonia and 3 ml. of tetrahydrofuran is added a solution of 300 mg. (0.513 mmole) of 6aβ,7,10,10aα-tetrahydro-6,6-dimethyl-3-[2-(5-phenyl-pentyloxy)]-1-(O-trifluoromethylsulfonyl)-6H-dibenzo[b,d]pyran9(8H)-one ethylene ketal in 2 ml. of tetrahydrofuran. After 1 hour the reaction is quenched with excess solid ammonium chloride. Ether is added and the mixture is slowly added to 100 ml. of saturated sodium chloride. The ether extract was washed once with saturated sodium chloride, dried over magnesium sulfate and evaporated to an oil. This oil is purified via preparative layer chromatography on silica gel (2 mm×20 cm×20 cm) eluted with 2:1 ether:cyclohexane to yield 65 mg. (28%) of the title product.

Treatment of the ketal with 1 N hydrochloric acid in the manner described in Example 16 followed by workup of the reaction mixture as described therein affords dl-6aβ,7,10,10aα-tetrahydro-1-amino-6,6-dimethyl-3-[2-(5-phenylpentyloxy)]-6H-dibenzo[b,d]pyran-9(8H)-one.

Similarly, the following compounds are prepared according to the procedure of Example 21 and the above procedure from appropriate reactants:

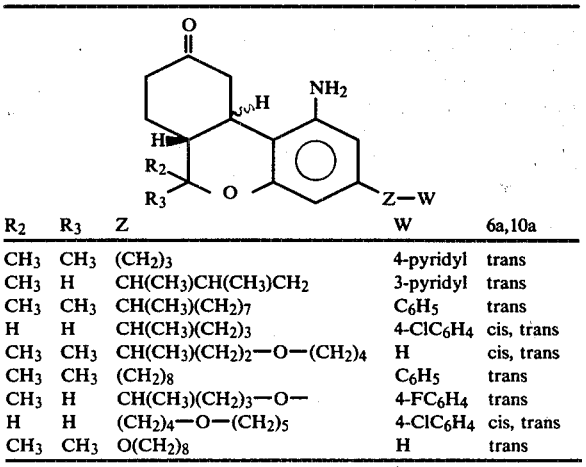

| R2 | R3 | Z | W | 6a,10a |
|---|---|---|---|---|
| CH3 | CH3 | (CH2)3 | 4-pyridyl | trans |
| CH3 | H | CH(CH3)CH(CH3)CH2 | 3-pyridyl | trans |
| CH3 | CH3 | CH(CH3)(CH2)7 | C6H5 | trans |
| H | H | CH(CH3)(CH2)3 | 4-ClC6H4 | cis, trans |
| CH3 | CH3 | CH(CH3)(CH2)2—O—(CH2)4 | H | cis, trans |
| CH3 | CH3 | (CH2)8 | C6H5 | trans |
| CH3 | H | CH(CH3)(CH2)3—O— | 4-FC6H4 | trans |
| H | H | (CH2)4—O—(CH2)5 | 4-ClC6H4 | cis, trans |
| CH3 | CH3 | O(CH2)8 | H | trans |

EXAMPLE 23 dl-6aβ,7,10,10aα-Tetrahydro-1-methylamino-6,6-dimethyl-3-[2-(5-phenylpentyloxy)]-6H-dibenzo[b,d]pyran-9(8H)-one Ethylene Ketal To a solution of 81 mg. (0.20 mmole) of dl-6aβ,7,10,10aα-tetrahydro-1-amino-6,6-dimethyl-3-[2-(5-phenylpentyloxy)]-6H-dibenzo[b,d]pyran-9(8H)-one and 12 mg. (0.2 mmole) acetic acid in 10 ml. of methanol is added 1.62 mg. (0.20 mmole) of formalin. The mixture is cooled in an ice bath and stirred for 15 minutes. It is then treated dropwise with sodium cyanoborohydride (14.15 mg. of 85%, 0.23 mmole) in methanol (15 ml.) over a period of 30 minutes. Upon completion of addition, the ice bath is removed and the reaction mixture stirred for 16 hours. It is then poured into a mixture of 150 ml. diethyl ether and 150 ml. saturated sodium bicarbonate. The ether phase is separated, dried over magnesium sulfate and evaporated. The oily residue is purified via preparative thin layer chromatography on three 20 cm×20 cm×0.5 mm silica gel plates eluted with 80% ether-pentane to give the title product as an oil.

Similarly, but substituting the appropriate aldehyde for formalin and using the appropriate dl-6a,7,10,10a-tetrahydro-6,6-$R_2R_3$-3-(Z-W)-6H-dibenzo[b,d]pyran-9(8H)-one ethylene ketals of Examples 16 and 20 as reactants affords compounds having the formula

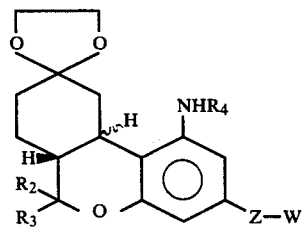

wherein $R_4$ is methyl, ethyl, n-propyl, isopropyl and n-butyl and $R_2$, $R_3$, Z and W are as defined in Examples 16 and 20.

Mild acid hydrolysis of the ketals according to the procedure of Example 16 affords the corresponding 9-oxo compound.

EXAMPLE 24 dl-6aβ,7,10,10aα-Tetrahydro-1-diethylamino-6,6-dimethyl-3-[2-(5-phenylpentyloxy)]-6H-dibenzo[b,d]pyran-9(8H)-one The procedure of Example 23 is repeated but using 2.21 mg. (0.50 mmole) of acetaldehyde in place of formalin, and 0.58 mmole of sodium cyanoborohydride to produce the title product.

Similarly, the compounds of Examples 16 and 20 are converted to 1-dialkylamino derivatives having the formula below by reaction with an excess of the appropriate aldehyde.

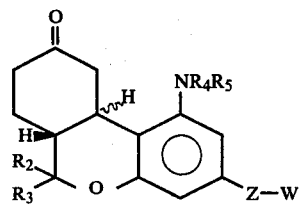

In the above formula $R_2$, $R_3$, Z and W are as defined in Examples 16 and 20, and $R_4$ and $R_5$ are each methyl, ethyl and n-butyl.

EXAMPLE 25 dl-6aβ,7,10,10aα-Tetrahydro-1-methylsulfonamido-6,6-dimethyl-3-[2-(5-phenylpentyloxy)]-6H-dibenzo[b,d]pyran-9(8H)-one Ethylene Ketal To 10 ml. of dry methylene chloride is added 205 mg. (0.50 mmole) of dl-6aβ,7,10,10aα-tetrahydro-1-amino-6,6-dimethyl-3-[2-(5-phenylpentyloxy)]-6H-dibenzo[b,d]pyran-9(8H)-one ethylene ketal, 0.76 ml. (0.55 mmole) of triethylamine and 58.4 mg. (0.51 mmole) of methanesulfonyl chloride and the resulting mixture stirred for 18 hours at room temperature. The reaction mixture is then poured into 50 ml. of water, the organic layer separated, washed with a saturated brine solution and dried over sodium sulfate. The solvent is removed under reduced pressure and the residue purified by chromatography on a silica gel column using acetone as solvent and eluate. The fractions containing the product are combined and concentrated in vacuo to dryness.

Treatment of the ketal with dilute (e.g. 1 N) hydrochloric acid according to the procedure of Example 16 affords the deketalized 9-oxo compound.

EXAMPLE 26

Following the procedure of Example 25, the compounds having the formula below are prepared from appropriate reactants of formula $R_3'SO_2Cl$ and appropriate compounds of Example 20.

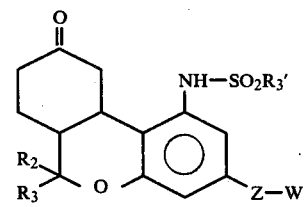

wherein Z, W, $R_2$ and $R_3$ are as defined in Example 20 and $R_3'$ is methyl, ethyl, n-propyl, n-butyl, n-pentyl, n-hexyl, benzyl, phenethyl, 3-phenylpropyl or 4-phenylbutyl.

EXAMPLE 27

Reduction of the compounds of Examples 23–26 according to the procedure of Example 17 affords compounds having the formula:

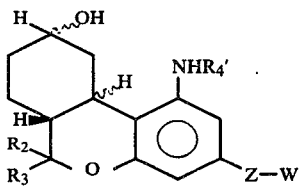

wherein the variables R₂, R₃, Z and W are as defined in said Examples and R₄' is R₄ or R₃' as defined in said Examples.

EXAMPLE 28

6aβ,7,10,10aα-Tetrahydro-6,6-dimethyl-1-formyl-3-[2-(5-phenylpentyloxy)]-6H-dibenzo[b,d]pyran-9(8H)-one To a 0° C. solution of 218 mg. (0.517 mmole) of 6aβ,7,10,10aα-tetrahydro-6,6-dimethyl-1-hydroxymethyl-3-[2-(5-phenylpentyloxy)]-6H-dibenzo[b,d]pyran-9(8H)-one in 2.5 ml. of dichloromethane is added 2.2 mg. (2.58 mmoles) of sodium acetate followed by 122 mg. (0.569 mmole) of pyridinium chlorochromate. The reaction mixture is stirred for 30 minutes, at the end of which time an additional 122 mg. portion of pyridinium chlorochromate is added and stirring continued for 30 minutes longer. To the reaction mixture is added one g. of solid sodium bicarbonate and 20 ml. of ether. The reaction mixture is stirred for 15 minutes and is then filtered through a small amount of silica gel. Evaporation of the filtrate gives a quantitative yield of the title product as an oil: $R_f = 0.36$ (silica gel, 50% ether-pentane).

Similarly, oxidation of 6aβ,7,10,10aβ-tetrahydro-6,6-dimethyl-1-hydroxymethyl-3-[2-(5-phenylpentyloxy)]-6H-dibenzo[b,d]pyran-9(8H)-one affords the corresponding 1-formyl derivative.

EXAMPLE 29

6aβ,7,10,10aα-Tetrahydro-6,6-dimethyl-3-[2-(5-phenylpentyloxy)]-6H-dibenzo[b,d]pyran-9(8H)-one A mixture of 217 mg. (0.517 mmole) of 6aβ,7,10,10aα-tetrahydro-6,6-dimethyl-1-formyl-3-[2-(5-phenylpentyloxy)]-6H-dibenzo[b,d]pyran-9(8H)-one and 478 mg. (0.517 mmole) of tris-triphenylphosphine rhodium chloride in 10 ml. of toluene is heated at reflux for 4 hours. The reaction mixture is cooled, diluted with ethanol and filtered. The filtrate is evaporated and purified via column chromatography on 100 g. of silica gel eluted with 30% ether-pentane to yield 109 mg. of oil. Further purification via preparative layer chromatography on three 20 cm×20 cm×0.5 mm silica gel plates eluted with 50% ether-pentane gives 88 mg. (44%) of the desired product as an oil.

PMR: $\delta_{CDCl_3}^{TMS}$ 1.25 (d, J=6 Hz, sidechain methyl), 1.47 and 1.67 (s, C-6 methyls), 4.30 (m, sidechain methine), 6.30 (bs, C-4 ArH), 6.38 (dd, J=8 and 2 Hz, C-2 ArH), 6.88 (d, J=8 Hz, C-1 ArH) and 7.15 (s, PhH).

IR: (CHCl₃) 1718, 1626 and 1585 cm⁻¹.

MS: m/e 392 (M+), 246 and 231.

Analysis: Calc'd for $C_{26}H_{32}O_3$: M+, 392.2351; Found: M+, 392.2384.

In like manner, the remaining products of Example 9 are converted by the procedure of Example 28 and the above procedure to compounds having the formula below wherein R₂, R₃, Z and W are as defined in Example 9 and the wavy line indicates the 6aβ,10aα- and 6aβ,10aβ-isomers.

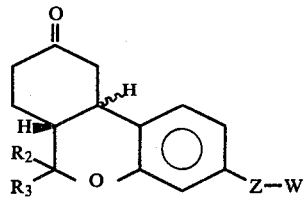

EXAMPLE 30

6aβ,7,10,10aα-Tetrahydro-6,6-dimethyl-3-[2-(5-phenylpentyloxy)]-6H-dibenzo[b,d]pyran-9(8H)-one A mixture of 1.3 g. (2.98 mmoles) of 6aβ,7,10,10aα-tetrahydro-6,6-dimethyl-3-[2-(5-phenylpentyloxy)]-6H-dibenzo[b,d]pyran-9(8H)-one ethylene ketal in 50 ml. tetrahydrofuran and 25 ml. 1 N hydrochloric acid is heated at reflux for one hour. The mixture is then cooled and added to 100 ml. saturated sodium chloride solution-200 ml. ether. The ether extract is separated, washed once with 100 ml. saturated sodium bicarbonate solution, dried over magnesium sulfate and evaporated to an oil. The oil is purified via column chromatography on 100 g. of silica gel eluted with 2:1 ether:cyclohexane to yield 1.01 g. (87%) of the title product. It is identical to the title product of Example 29.

EXAMPLE 31

6aβ,7,8,9,10,10aα-Hexahydro-6,6-dimethyl-3-[2-(5-phenylpentyloxy)]-6H-dibenzo[b,d]pyran-9β-ol and the 9α isomer To a 0° C. solution of 479 mg. (1.22 mmole) of 6aβ,7,10,10aα-tetrahydro-6,6-dimethyl-3-[2-(5-phenylpentyloxy)]-6H-dibenzo[b,d]pyran-9(8H)-one in 10 ml. of ethanol is added 464 mg. (12.2 mmoles) of sodium borohydride. The reaction mixture is stirred for 25 minutes and is then added to 200 ml. ether-100 ml. saturated sodium chloride solution. The ether extract is separated, washed twice with 100 ml. portions of saturated sodium chloride solution, dried over magnesium sulfate and evaporated to an oil. The oil is purified via column chromatography on 100 g. of silica gel eluted with 2:1 ether:cyclohexane to yield in order of elution 6aβ,7,8,9,10,10aα-hexahydro-6,6-dimethyl-3-[2-(5-phenylpentyloxy)]-6H-dibenzo[b,d]pyran-9α-ol (45 mg., 9%, as an oil):

PMR: $\delta_{CDCl_3}^{TMS}$ 1.20 (s, C-6 methyl), 1.28 (d, J=6 Hz, sidechain methyl), 4.35 (m, C-9 methine and sidechain methine), 6.38 (bs, C-4 ArH), 6.48 (dd, J=8 and 2 Hz, C-2 ArH), 7.10 (d, J=8 Hz, C-1 methyl) and 7.28 (s, PhH).

IR: (CHCl₃)

MS: m/e 397 (M+), 248, 230, 215 and 187

Analysis: Calc'd for $C_{26}H_{34}O_3$: M+, 394.2508 Found: M+, 394.2435;

15 mg. (3%) of mixed fractions and 6aβ,7,8,9,10,10aα-hexahydro-6,6-dimethyl-3-[2-(5-phenylpentyloxy)]-6H-dibenzo[b,d]pyran-9β-ol (417 mg., 87%, as an oil):

PMR: $\delta_{CDCl_3}^{TMS}$ 1.15 (s, C-6 methyl), 1.28 (d, J=6 Hz, sidechain methyl), 1.42 (s, C-6 methyl), 3.85 (bm, C-9 methine), 4.35 (m, sidechain methine), 6.42 (bs, C-4 ArH), 6.50 (dd, J=8 and 2 Hz, C-2 ArH), 7.13 (d, J=8 Hz, C-1 ArH) and 7.28 (s, PhH).

IR: (CHCl$_3$) 3559, 3413, 1623 and 1580 cm$^{-1}$.
MS: m/e 394 (M+), 379, 248, 288 and 230.
Analysis: Calc'd for C$_{26}$H$_{34}$O$_3$: M+, 394.2508 Found: M+, 394.2484;

The remaining compounds of Example 29 are similarly reduced to their isomeric alcohols having the formula:

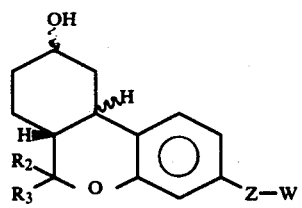

EXAMPLE 32

2,2,5-Trimethyl-7-[2-(5-phenylpentyloxy)]-chroman-4-one

A mixture of 20.0 g. (97.0 mmoles) of 2,2,5-trimethyl-7-hydroxychroman-4-one, 25.9 g. (107 mmoles) of 2-(5-phenylpentyl)methanesulfonate and 27.6 g. (200 mmoles) of anhydrous potassium carbonate in 125 ml. of dimethylformamide is heated at 80°-85° C. for 5.5 hours. The reaction mixture is cooled and added to 500 ml. ice water and 500 ml. ether. The organic phase is separated, washed once with 500 ml. ice water-50 ml. concentrated potassium carbonate solution and twice with 300 ml. portions of cold water. The ether extract is dried over magnesium sulfate and evaporated to give a quantitative yield of the title product as an oil.

PMR: $\delta_{CDCl_3}{}^{TMS}$ 1.26 (d, J=6 Hz, sidechain methyl), 1.43 (s, C-2 -methyls), 1.71 (m, two sidechain methylenes), 2.60 (s, C-3 methylene), 2.60 (m, sidechain benzylic methylene), 2.63 (s, C-5 methyl), 4.42 (m, sidechain methine), 6.25 (m, two ArH) and 7.21 (s, PhH).

IR: (CHCl$_3$) 1681, 1667, 1613, 1600 and 1563 cm$^{-1}$.
MS: m/e 352 (M+), 206 and 191.

EXAMPLE 33

In like manner, the following compounds are prepared from the appropriate 2-R$_2$,R$_3$-7-hydroxy-5-R$_1$-chroman-4-one and the appropriate mesylate CH$_3$SO$_2$-Z-W wherein Z is —O—(alk$_2$)$_n$-W.

| R$_1$'' | R$_2$ | R$_3$ | (alk$_2$) | W |
|---|---|---|---|---|
| CH$_3$ | CH$_3$ | CH$_3$ | CH$_2$ | H |
| H, CH$_3$ | CH$_3$ | CH$_3$ | CH$_2$C(CH$_3$)$_2$(CH$_2$)$_5$ | H |
| H, CH$_3$ | CH$_3$ | CH$_3$ | CH$_2$CH(CH$_3$)(CH$_2$)$_2$CH(CH$_3$)(CH$_2$)$_2$ | H |
| H, CH$_3$ | CH$_3$ | H | (CH$_2$)$_2$CH(CH$_3$)CH$_2$CH(CH$_3$)CH$_2$ | H |
| H, CH$_3$ | H | H | CH(CH$_3$)(CH$_2$)$_2$C(CH$_3$)$_2$CH$_2$ | H |
| H, CH$_3$ | H | CH$_3$ | (CH$_2$)$_7$ | C$_6$H$_5$ |
| H, CH$_3$ | H | H | CH(CH$_3$)(CH$_2$)$_5$ | C$_6$H$_5$ |
| H, CH$_3$ | H | CH$_3$ | CH(CH$_3$)CH$_2$ | 2-pyridyl |
| H, CH$_3$ | H | H | (CH$_2$)$_2$ | 4-pyridyl |
| H, CH$_3$ | CH$_3$ | CH$_3$ | (CH$_2$)$_3$ | 3-pyridyl |
| H, CH$_3$ | CH$_3$ | CH$_3$ | (CH$_2$)$_3$ | 4-FC$_6$H$_4$ |
| H, CH$_3$ | H | H | (CH$_2$)$_3$ | 4-ClC$_6$H$_4$ |
| H, CH$_3$ | H | H | CH(CH$_3$)(CH$_2$)$_2$ | 2-pyridyl |
| H, CH$_3$ | CH$_3$ | CH$_3$ | CH(CH$_3$)(CH$_2$)$_3$ | 4-pyridyl |
| H, CH$_3$ | CH$_3$ | CH$_3$ | CH(C$_2$H$_5$)(CH$_2$)$_2$ | 4-pyridyl |
| H, CH$_3$ | CH$_3$ | H | CH(CH$_3$)(CH$_2$)$_2$ | 4-ClC$_6$H$_4$ |
| H, CH$_3$ | CH$_3$ | CH$_3$ | — | C$_6$H$_5$ |
| H, CH$_3$ | CH$_3$ | CH$_3$ | — | 4-FC$_6$H$_4$ |
| H, CH$_3$ | CH$_3$ | H | — | 4-ClC$_6$H$_4$ |
| H, CH$_3$ | CH$_3$ | CH$_3$ | — | 4-pyridyl |
| H, CH$_3$ | CH$_3$ | CH$_3$ | — | 3-pyridyl |

EXAMPLE 34

6aβ,7,10,10aα-Tetrahydro-6,6-dimethyl-3-[2-(5-phenylpentyloxy)]-6H-dibenzo[b,d]pyran-1-carboxylic acid-9(8H)-one To a refluxing solution of 176 mg. (0.419 mmole) of 6aβ,7,10,10aα-tetrahydro-6,6-dimethyl-3-[2-(5-phenylpentyloxy)-6H-dibenzo[b,d]pyran-1-carboxaldehyde-9(8H)-one in 3 ml. of acetone is added slowly 0.838 ml. of a 0.5 M potassium permanganate solution. After 15 minutes an additional 0.6 ml. portion of 0.5 M potassium permanganate is added. The reaction is refluxed 30 minutes longer and is then filtered through diatomaceous earth. The filtrate is evaporated and the residue dissolved in 200 ml. ether - 50 ml. saturated sodium chloride - 2 ml. 1 N hydrochloric acid. The organic phase is separated, dried over magnesium sulfate and evaporated to yield 118 mg. (65%) of the title product as a solid, white foam.

IR: (CHCl$_3$) 3636-2222, 1721, 1618 and 1585 cm$^{-1}$.
PMR: $\delta_{CDCl_3}{}^{TMS}$ 1.22 (s, C-6 methyl), 1.32 (d, J=6 Hz, sidechain methyl), 1.53 (s, C-6 methyl), 4.20 (m, sidechain methine), 6.58 (d, J=2 Hz, C-4 ArH), 7.12 (d, J=2 Hz, C-2 ArH), 7.30 (s, PhH) and 10.00 (bs, COOH).
MS: m/e 436 (M⊕), 290, 275 and 272.

EXAMPLE 35

6aβ,7,8,9,10,10aα-Hexahydro-6,6-dimethyl-3-[2-(5-phenylpentyloxy)]-6H-dibenzo[b,d]pyran-1-carboxylic acid-9-β-ol to a −15° C. solution of 65 mg. (0.149 mmole) of 6aβ,7,10,10aα-tetrahydro-6,6-dimethyl-3-[2-(5-phenylpentyloxy)]-6H-dibenzo[b,d]pyran-1-carboxylic acid- 9(8H)-one in 1 ml. of methanol is added 15 mg. (0.395 mmole) of sodium borohydride. The reaction is stirred for 20 minutes and is then added to 150 ml. ether - 50 ml. saturated sodium chloride. The ether extract is dried over magnesium sulfate and evaporated. The residue is crystallized in pentane to yield 45 mg. (69%) of the title product.

MP: 105°–110° C.

IR: (CHCl$_3$) 3636–2105, 3279, 1689, 1608 and 1577 cm$^{-1}$.

MS: m/e 438 (M⊕), 420, 292, 274 and 259.

EXAMPLE 36

2,2,5-Trimethyl-3-(3-oxobutyl)-7-[2-(5-phenylpentyloxy)]chroman-4-one

To 6.82 g. (0.284 mole) of dry sodium hydride is added over a 30 minute period, with stirring, 20.0 g. (56.8 mmoles) of 2,2,5-trimethyl-7-[2-(5-phenylpentyloxy)]chroman-4-one in 100 ml. of ethyl formate. The reaction mixture is then stirred for two hours and maintained at a temperature of 0° C.–15° C. with cooling. The reaction mixture is cooled to 0° C. and added to 500 ml. ice cold ether and 200 ml. of ice cold 3.6 N hydrochloric acid. The organic phase is separated, washed with three 200 ml. portions of ice water, dried over magnesium sulfate for 30 minutes at 0° C. and evaporated (t≦20° C.) to yield 2,2,5-trimethyl-3-hydroxymethylene-7-[2-(5-phenylpentyloxy)]chroman-4-one as an oil. Without further purification this oil is dissolved in 200 ml. of methanol followed by the addition of 16 ml. (197 mmoles) of methyl vinyl ketone and 8 ml. (57.5 mmoles) of triethylamine. The reaction mixture is stirred for 16 hours at room temperature and is then evaporated (t≦20° C.) to yield 2,2,5-trimethyl-3-formyl-3-oxobutyl)-7-[2-(5-phenylpentyloxy)]chroman-4-one as an oil. Without further purification this oil is dissolved in 100 ml. of methanol, cooled to 0° C. and 50 ml. of 2 N potassium hydroxide in methanol added. The reaction mixture is stirred for 15 minutes at 0° C. and is then evaporated (t≦20° C.). The residue is added to 200 ml. of cold 15% potassium carbonate and 500 ml. ether. The organic phase is separated and washed twice with 200 ml. portions of cold 15% potassium carbonate solution, dried over magnesium sulfate and evaporated to an oil. This oil is purified via column chromatography on 750 g. of silica gel eluted with 30% ether-pentane to yield 16.5 g. (69%) of 2,2,5-trimethyl-3-(3-oxobutyl)-7-[2-(5-phenylpentyloxy)]chroman-4-one.

2,2,5-Trimethyl-3-hydroxymethylene-7-[2-(5-phenylpentyloxy)]chroman-4-one:

PMR: $\delta_{CDCl_3}^{TMS}$ 1.29 (d, J=6 Hz, sidechain methyl), 1.55 (s, C-2 methyls), 1.72 (m, two sidechain methylenes), 2.65 (s, C-5 methyl), 2.65 (m, sidechain benzylic methylene), 4.42 (m, sidechain methine), 6.23 (d, J=2 Hz, C-8 ArH), 6.35 (d, J=2 Hz, C-6 ArH), 7.25 (s, PhH), 7.73 (s, C-2' vinyl proton) and 15.5 (bs, OH).

2,2,5-Trimethyl-3-formyl-3-(3-oxobutyl)-7-[2-(5-phenylpentyloxy)]chroman-4-one:

PMR: $\delta_{CDCl_3}^{TMS}$ 1.35 (d, J=6 Hz, sidechain methyl), 1.43 and 1.56 (s, C-2 methyls), 2.08 (s, COCH$_3$), 2.66 (s, C-5 methyl), 4.53 (m, sidechain methine), 6.33 (d, J=2 Hz, C-8 ArH), 6.46 (d, J=2 Hz, C-6 ArH), 7.35 (s, PhH) and 9.91 (s, CHO).

IR: (CCl$_4$) 1715, 1653, 1595 and 1565 cm$^{-1}$.

MS: m/e 450 (M+), 422, 407 and 261.

UV: $\lambda_{max}^{EtOH}$ ($\epsilon$) 321 (5,120), 283 (15,500), 230 (8,320) and 223 (9,260).

2,2,5-Trimethyl-3-(3-oxobutyl)-7-[2-(5-phenylpentyloxy)]chroman-4-one:

PMR: $\delta_{CDCl_3}^{TMS}$ 1.31 (d, J=6 Hz, sidechain methyl), 1.38 and 1.46 (s, C-2 methyls), 2.15 (s, COCH$_3$), 2.60 (s, C-5 methyl), 4.43 (m, sidechain methine), 6.21 (d, J=2 Hz, C-8 ArH), 6.31 (d, 2 Hz, C-6 ArH) and 7.25 (s, PhH).

IR: (CHCl$_3$) 1724, 1678, 1605 and 1565 cm$^{-1}$.

MS: 422 (M+), 407, 276 and 261.

EXAMPLE 37

6a,7-Dihydro-3-[2-(5-phenylpentyloxy)]-1,6,6-trimethyl-6H-dibenzo[b,d]pyran-9(8H)-one A solution of 3.0 g. (7.1 mmoles) of 2,2,5-trimethyl-3-(3-oxobutyl)-7-[2-(5-phenylpentyloxy)]chroman-4-one in one liter of 1 N methanolic potassium hydroxide is heated at reflux for 15 hours. The reaction mixture is cooled and evaporated to a thick oil which is added to 500 ml. ice water-500 ml. ether. The ether extract is washed once with 250 ml. of cold water. The total aqueous phase is extracted again with 250 ml. of ether and the extract washed once with 200 ml. of cold water. The combined extract is dried over magnesium sulfate and evaporated to an oil. This oil is purified via column chromatography on 300 g. of silica gel eluted with 2:1 ether:pentane to yield 1.94 g. (67%) of the title product as an oil.

PMR: $\delta_{CDCl_3}^{TMS}$ 1.16 (s, C-6 -methyl), 1.25 (d, J=6 Hz, sidechain methyl), 1.52 (s, C-6 methyl), 2.52 (s, C-1 methyl), 4.38 (m, sidechain methine), 6.25 (d, J=2 Hz, C-4 ArH), 6.38 (d, J=2 Hz, C-2 ArH), 6.52 (d, J=2 Hz, C-10 vinyl H) and 7.27 (s, PhH).

IR: (CHCl$_3$) 1650, 1603, 1582 and 1565 cm$^{-1}$.

MS: m/e 404 (M+), 389, 376, 297, 258 and 243.

EXAMPLE 38

6a$\beta$,7,10,10a$\alpha$-Tetrahydro-3-[2-(5-phenylpentyloxy)]-1,6,6-trimethyl-6H-dibenzo[b,d]pyran-9(8H)-one, and the 6a$\beta$, 10a$\beta$ isomer To a −78° C. solution of 63 mg. (9 mmoles) of lithium in 100 ml. of ammonia and 20 ml. of tetrahydrofuran is slowly added a solution of 800 mg. (1.98 mmole) of 6a,7-dihydro-3-[2-(5-phenylpentyloxy)]-1,6,6-trimethyl-6H-dibenzo[b,d]pyran-9(8H)-one in 15 ml. of tetrahydrofuran. During the addition an additional 91 mg. (13 mmoles) of lithium is added to maintain a blue color in the reaction mixture. The reaction mixture is stirred an additional 10 minutes and is then quenched with excess solid ammonium chloride. The ammonia is allowed to evaporate and the residue added to 100 ml. of water and 200 ml. ether. The ether phase is dried over magnesium sulfate and evaporated to an oil which is purified via column chromatography on 300 g. of silica gel eluted with 40% ether-petroleum ether to yield in order of elution 344 mg. (43%) of 6a$\beta$,7,10,10a$\alpha$-tetrahydro-3-[2-(5-phenylpentyloxy)]-1,6,6-trimethyl-6H-dibenzo[b,d]pyran-9(8H)-one as an oil:

PMR: $\delta_{CDCl_3}^{TMS}$ 1.07 (s, C-6 methyl), 1.25 (d, J=6 Hz, sidechain methyl), 1.48 (s, C-6 methyl), 2.28 (s, C-1 methyl), 4.27 (m, sidechain methine), 6.23 (m, C-2 and 4 ArH) and 7.20 (s, PhH).

IR: (CHCl$_3$) 1709, 1608 and 1575 cm$^{-1}$.

MS: m/e 406 (M+), 391, 260 and 245;

38 mg. (5%) of mixed fractions, and then 270 mg. (34%) of 6a$\beta$,7,10, 10a$\beta$-tetrahydro-3-[2-(5-phenylpentyloxy)]-1,6,6-trimethyl-6H-dibenzo[b,d]pyran-9(8H)-one as an oil:

The filtrate is concentrated under vacuum to an oily residue which is chromatographed over silica gel (1500 g.) and eluted with benzene:hexane solutions of increasing benzene concentration beginning with 40:60 and ending with 100% benzene. Concentration of appropriate fractions gives an oily residue which is crystallized from hexane.

In like manner, ethyl 3-(3-methoxyphenyl)crotonate is prepared from 3-methoxyacetophenone (43.1 g.) and carbethoxymethylene triphenylphosphorane (200 g.).

PREPARATION G

3-(3-Benzyloxyphenyl)-1-butanol

A solution of ethyl 3-(3-benzyloxyphenyl)crotonate (17.7 g., 60 mM) in ether (250 ml.) is added to a mixture of lithium aluminum hydride (3.42 g., 90 mM) and ether (250 ml.). Aluminum chloride (0.18 g., 1.35 mM) is added and the mixture refluxed for 12 hours and then cooled. Water (3.4 ml.), sodium hydroxide (3.4 ml. of 6 N) and water (10 ml.) are then added successively to the reaction mixture. The inorganic salts which precipitate are filtered off and the filtrate is then concentrated in vacuo to give the desired alcohol as an oil.

In like manner, ethyl 3-(3-methoxyphenyl)crotonate is reduced to 3-(3-methoxyphenyl)-1-butanol.

PREPARATION H

3-(3-Benzyloxyphenyl)butyl Tosylate

Tosyl chloride (9.8 g., 51 mM) is added to a solution of 3-(3-benzyloxyphenyl)-1-butanol (12.8 g., 50 mM) in pyridine (90 ml.) at $-45°$ C. The reaction mixture is held at $-35°$ C. for 18 hours and is then diluted with cold 2 N hydrochloric acid (1500 ml.) and extracted with ether (5×250 ml.). The combined extracts are washed with saturated sodium chloride solution (4×250 ml.) and then dried ($Na_2SO_4$). Concentration of the dried extract affords the product as an oil. It is crystallized by treatment with ether-hexane.

PREPARATION I

3-(3-Benzyloxyphenyl)-1-phenoxybutane

A solution of phenol (4.56 g., 48.6 mM) in dimethylformamide (40 ml.) is added under a nitrogen atmosphere to a suspension of sodium hydride (2.32 g., 48.6 mM of 50% previously washed with pentane) in dimethylformamide (70 ml.) at 60° C. The reaction mixture is stirred for one hour at 60°–70° C., after which a solution of 3-(3-benzyloxyphenyl)butyl tosylate (19.46 g., 46.3 mM) in dimethylformamide (80 ml.) is added. The reaction mixture is stirred at 80° C. for a half hour and is then cooled to room temperature, diluted with cold water (2500 ml.) and extracted with ether (4×400 ml.). The combined extracts are washed successively with cold 2 N hydrochloric acid (2×300 ml.) and saturated sodium chloride solution (3×300 ml.) and the dried ($Na_2SO_4$). Removal of the solvent under reduced pressure affords the product as an oil. The oily residue is dissolved in benzene and filtered through silica gel (100 g.). Concentration of the filtrate under pressure gives the product as an oil.

Repetition of Procedures F through I, but using the appropriate reactant of formula

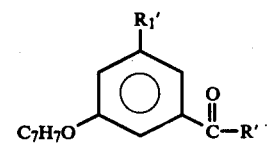

wherein R' is hydrogen, methyl or ethyl and $R_1'$ is hydrogen, methyl or 2-phenylethenyl, the appropriate carbethoxy (or carbomethoxy) alkylidene triphenyl phosphorane; and the appropriate alcohol, phenol or hydroxypyridine as reactants affords the following compounds:

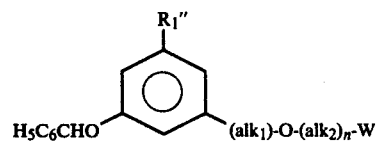

For convenience, the various values of $R_1''$ and W for given values of —(alk$_1$)-O-(alk$_2$)$_n$— are collectively tabulated.

| $R_1''$ | alk$_1$ | alk$_2$ | n | W |
|---|---|---|---|---|
| PE, H, CH$_3$ | (CH$_2$)$_3$ | — | 0 | C$_6$H$_5$, 4-FC$_6$H$_4$, 4-pyridyl |
| PE, H, CH$_3$ | (CH$_2$)$_3$ | (CH$_2$)$_3$ | 1 | C$_6$H$_5$, H, 4-ClC$_6$H$_4$, 4-pyridyl |
| H | (CH$_2$)$_3$ | CH(CH$_3$) | 1 | C$_6$H$_5$, 4-FC$_6$H$_4$, 2-pyridyl |
| H | (CH$_2$)$_3$ | CH(CH$_3$)(CH$_2$)$_2$ | 1 | 4-pyridyl, H, 4-ClC$_6$H$_4$ |
| PE, H, CH$_3$ | CH(CH$_3$)(CH$_2$)$_2$ | — | 0 | C$_6$H$_5$, 4-pyridyl |
| H | CH(CH$_3$)(CH$_2$)$_2$ | (CH$_2$)$_2$ | 1 | C$_6$H$_5$, 4-FC$_6$H$_4$, 4-pyridyl |
| PE, H | CH(CH$_3$)(CH$_2$)$_2$ | (CH$_2$)$_4$ | 1 | C$_6$H$_5$, 4-pyridyl, H |
| H, CH$_3$ | CH(CH$_3$)(CH$_2$)$_2$ | CH(CH$_3$)(CH$_2$)$_2$ | 1 | C$_6$H$_5$, 4-ClC$_6$H$_4$, H |
| H | CH(CH$_3$)(CH$_2$)$_2$ | CH$_2$CH(C$_2$H$_5$) | 1 | C$_6$H$_5$ |
| H, CH$_3$ | CH(CH$_3$)(CH$_2$)$_3$ | (CH$_2$)$_4$ | 1 | C$_6$H$_5$, 4-FC$_6$H$_4$, 2-pyridyl |
| PE, H | CH(C$_2$H$_5$)(CH$_2$)$_2$ | — | 0 | C$_6$H$_5$, 4-pyridyl |
| PE | (CH$_2$)$_8$ | — | 0 | C$_6$H$_5$ |
| H | CH(C$_2$H$_5$)(CH$_2$)$_2$ | (CH$_2$)$_2$CH(CH$_3$) | 1 | C$_6$H$_5$, 4-FC$_6$H$_4$ |
| PE, H, CH$_3$ | (CH$_2$)$_4$ | — | 0 | C$_6$H$_5$, 4-FC$_6$H$_4$, 4-ClC$_6$H$_4$, 4-pyridyl |
| PE, CH$_3$ | (CH$_2$)$_4$ | CH$_2$ | 1 | C$_6$H$_5$, 4-FC$_6$H$_4$, 4-pyridyl, 3-pyridyl |
| CH$_3$ | (CH$_2$)$_4$ | CH(CH$_3$)CH$_2$ | 1 | C$_6$H$_5$, H, 2-pyridyl, 4-FC$_6$H$_4$ |
| H | (CH$_2$)$_4$ | (CH$_2$)$_5$ | 1 | C$_6$H$_5$, 4-pyridyl, 4-ClC$_6$H$_4$ |

PREPARATION J

3-(3-Hydroxyphenyl)-1-phenoxybutane

A solution of 3-(3-benzyloxyphenyl)-1-phenoxybutane (11.2 g., 33.5 mM) in a mixture of ethyl acetate (110 ml.), ethanol (110 ml.) and concentrated hydrochloric acid (0.7 ml.) is hydrogenated for 2 hours under 60 p.s.i. hydrogen in the presence of 10% palladium-on-carbon (1.5 g.). Removal of the catalyst by filtration and concentration of the filtrate gives an oil. The oil is purified by chromatography on silica gel (100 g.) and eluting with benzene-ethyl acetate consisting of 0–10% ethyl acetate. The middle fractions are combined and concentrated to give the title product as an oil.

PREPARATION K

1-Bromo-3-(3-methoxyphenyl)butane

A solution of phosphorous tribromide (5.7 ml., 0.06 mole) in ether (30 ml.) is added to a solution of 3-(3-methoxyphenyl)-1-butanol (25.8 g., 0.143 mole) in ether (20 ml.) at −5° C. to −10° C. and the reaction mixture stirred at −5° C. to −10° C. for 2.5 hours. It is then warmed to room temperature and stirred for an additional 30 minutes. The mixture is poured over ice (200 g.) and the resulting mixture extracted with ether (3×50 ml.). The combined extracts are washed with 5% sodium hydroxide solution (3×50 ml.), saturated sodium chloride solution (1×50 ml.) and dried ($Na_2SO_4$). Removal of the ether and vacuum distillation of the residue affords the title product.

The following compounds are prepared from the appropriate

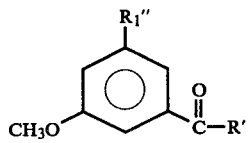

reactant wherein $R_1''$ is hydrogen or methyl and $R'$ is hydrogen, methyl or ethyl and the appropriate carbethoxyalkylidene triphenylphosphorane by the procedures of Preparations H, F, G and K.

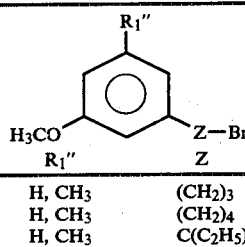

| $R_1''$ | Z |
|---|---|
| H, CH3 | (CH2)3 |
| H, CH3 | (CH2)4 |
| H, CH3 | C(C2H5)CH2 |

PREPARATION L

4-(3-Hydroxyphenyl)-1-(4-pyridyl)pentane

A mixture of 3-(3-methoxyphenyl)butyl triphenylphosphonium bromide (17.9 g., 35.4 mmoles) in dimethylsulfoxide (50 ml.) is added to 4-pyridinecarboxaldehyde (3.79 g., 35.4 mmoles) in tetrahydrofuran (40 ml.). The resulting mixture is then added dropwise to a slurry of 50% sodium hydride (1.87 g., 39 mmoles) in tetrahydrofuran (20 ml.) under a nitrogen atomsphere at 0°-5° C. Following completion of addition, the mixture is stirred for one hour at 0°-5° and then concentrated under reduced pressure. The concentrate is diluted with water (200 ml.) and then acidified with 6 N HCl. The aqueous acid solution is extracted with benzene (4×50 ml.). It is then made basic and extracted with ethyl acetate (3×50 ml.). Evaporation of the combined extracts after drying (MgSO4) affords 4-(3-methoxyphenyl)-1-(4-pyridyl)-1-pentene as an oil.

Catalytic hydrogenation of the thus-produced pentene derivative in ethanol (250 ml.) using palladium-on-charcoal (1 g. of 10%) at 45 p.s.i. and concentrated hydrochloric acid (1 ml.) gives 4-(3-methoxyphenyl)-1-(4-pyridyl)pentane in quantitative yield.

The pentane derivative thus obtained is demethylated by heating a mixture of the compound (6.38 g., 25 mmoles) and pyridine hydrochloride (35 g.) under a nitrogen atmosphere at 210° C. for 8 hours. The hot mixture is poured into water (40 ml.) and the resulting solution made basic with 6 N sodium hydroxide. Water and pyridine are removed by distillation in vacuo. Ethanol (50 ml.) is added to the residue and the inorganic salts which precipitate are filtered off. The filtrate is concentrated in vacuo and the residue chromatographed on silica gel (150 g.) using as eluting agents 5% ethanol/benzene (4 liters), 10% ethanol/benzene (1 liter), 13% ethanol/benzene (1 liter) and 16% ethanol/benzene (5 liters). The product is isolated as a glassy solid by concentration of appropriate fractions of the eluate.

The 3-(3-methoxyphenyl)butyltriphenylphosphonium bromide is prepared by refluxing a mixture of 1-bromo-3-(3-methoxyphenyl)butane (19.09 g., 78.5 mmoles) and triphenyl phosphine (20.5 g., 78.5 mmoles) in xylene (60 ml.) for 18 hours. The reaction mixture is then cooled to room temperature and filtered. The filter cake is washed with ether and dried in a vacuum desicator to give the products.

Repetition of this procedure but using the appropriate bromo-(3-methoxyphenyl)alkane and the appropriate phenolic aldehyde or ketone affords the following compounds.

| $R_1''$ | Z | W |
|---|---|---|
| H, CH3 | (CH2)3 | 2-pyridyl |
| H | (CH2)3 | 3-pyridyl |
| H, CH3 | (CH2)3 | 4-pyridyl |
| H, CH3 | (CH2)4 | 2-pyridyl |
| CH3 | (CH2)4 | 4-pyridyl |
| H, CH3 | CH2CH(CH3)CH2 | 2-pyridyl |
| H | CH(CH3)CH(CH3)CH2 | 3-pyridyl |
| H, CH3 | CH(CH3)CH(CH3)CH2 | 4-pyridyl |
| H, CH3 | CH(CH3)(CH2)3 | 3-pyridyl |
| H | CH(CH3)CH(C2H5)CH2 | 4-pyridyl |
| CH3 | CH(C2H5)(CH2)2 | 4-pyridyl |
| H | CH(C2H5)(CH2)3 | 3-pyridyl |
| CH3 | CH(C2H5)CH(C2H5)CH2 | 4-pyridyl |
| CH3 | (CH2)6 | C6H5 |
| CH3 | (CH2)8 | C6H5 |
| H | CH(CH3)(CH2)7 | C6H5 |
| H, CH3 | CH(CH3)(CH2)3 | 4-FC6H4 |
| H | C(CH3)2(CH2)3 | C6H5 |
| H | CH(CH3)(CH2)3 | 4-ClC6H4 |
| CH3 | CH(CH3)(CH2)4 | 4-ClC6H4 |
| H | CH(CH3)(CH2)2 | 4-FC6H4 |
| H, CH3 | CH(CH3)CH(CH3)(CH2)5 | H |
| H, CH3 | C(CH3)2(CH2)6 | H |
| H, CH3 | (CH2)5 | H |

PREPARATION M

3-Methoxy-5-(2-phenylethenyl)acetophenone

Methyl lithium (501 ml. of a 2 molar solution, 1.00 M) is added over a period of 2.0 hours under a nitrogen atmosphere to a rapidly stirring solution of 5-methoxy-3-stilbene carboxylic acid (115.1 g., 0.50 M) in ether (200 ml.) - tetrahydrofuran (1200 ml.) at 15°-20° C. The The filtrate is concentrated under vacuum to an oily residue which is chromatographed over silica gel (1500 g.) and eluted with benzene:hexane solutions of increasing benzene concentration beginning with 40:60 and ending with 100% benzene. Concentration of appropriate fractions gives an oily residue which is crystallized from hexane.

In like manner, ethyl 3-(3-methoxyphenyl)crotonate is prepared from 3-methoxyacetophenone (43.1 g.) and carbethoxymethylene triphenylphosphorane (200 g.).

PREPARATION G

3-(3-Benzyloxyphenyl)-1-butanol

A solution of ethyl 3-(3-benzyloxyphenyl)crotonate (17.7 g., 60 mM) in ether (250 ml.) is added to a mixture of lithium aluminum hydride (3.42 g., 90 mM) and ether (250 ml.). Aluminum chloride (0.18 g., 1.35 mM) is added and the mixture refluxed for 12 hours and then cooled. Water (3.4 ml.), sodium hydroxide (3.4 ml. of 6 N) and water (10 ml.) are then added successively to the reaction mixture. The inorganic salts which precipitate are filtered off and the filtrate is then concentrated in vacuo to give the desired alcohol as an oil.

In like manner, ethyl 3-(3-methoxyphenyl)crotonate is reduced to 3-(3-methoxyphenyl)-1-butanol.

PREPARATION H

3-(3-Benzyloxyphenyl)butyl Tosylate

Tosyl chloride (9.8 g., 51 mM) is added to a solution of 3-(3-benzyloxyphenyl)-1-butanol (12.8 g., 50 mM) in pyridine (90 ml.) at −45° C. The reaction mixture is held at −35° C. for 18 hours and is then diluted with cold 2 N hydrochloric acid (1500 ml.) and extracted with ether (5×250 ml.). The combined extracts are washed with saturated sodium chloride solution (4×250 ml.) and then dried ($Na_2SO_4$). Concentration of the dried extract affords the product as an oil. It is crystallized by treatment with ether-hexane.

PREPARATION I

3-(3-Benzyloxyphenyl)-1-phenoxybutane

A solution of phenol (4.56 g., 48.6 mM) in dimethylformamide (40 ml.) is added under a nitrogen atmosphere to a suspension of sodium hydride (2.32 g., 48.6 mM of 50% previously washed with pentane) in dimethylformamide (70 ml.) at 60° C. The reaction mixture is stirred for one hour at 60°–70° C., after which a solution of 3-(3-benzyloxyphenyl)butyl tosylate (19.46 g., 46.3 mM) in dimethylformamide (80 ml.) is added. The reaction mixture is stirred at 80° C. for a half hour and is then cooled to room temperature, diluted with cold water (2500 ml.) and extracted with ether (4×400 ml.). The combined extracts are washed successively with cold 2 N hydrochloric acid (2×300 ml.) and saturated sodium chloride solution (3×300 ml.) and the dried ($Na_2SO_4$). Removal of the solvent under reduced pressure affords the product as an oil. The oily residue is dissolved in benzene and filtered through silica gel (100 g.). Concentration of the filtrate under pressure gives the product as an oil.

Repetition of Procedures F through I, but using the appropriate reactant of formula

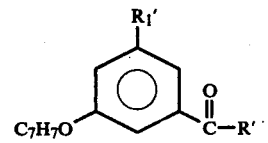

wherein R′ is hydrogen, methyl or ethyl and $R_1'$ is hydrogen, methyl or 2-phenylethenyl, the appropriate carbethoxy (or carbomethoxy) alkylidene triphenyl phosphorane; and the appropriate alcohol, phenol or hydroxypyridine as reactants affords the following compounds:

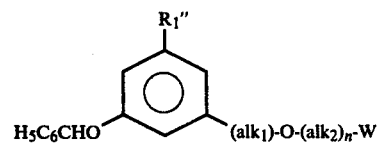

For convenience, the various values of $R_1''$ and W for given values of —(alk$_1$)-O-(alk$_2$)$_n$— are collectively tabulated.

| $R_1''$ | alk$_1$ | alk$_2$ | n | W |
|---|---|---|---|---|
| PE, H, CH$_3$ | (CH$_2$)$_3$ | — | 0 | C$_6$H$_5$, 4-FC$_6$H$_4$, 4-pyridyl |
| PE, H, CH$_3$ | (CH$_2$)$_3$ | (CH$_2$)$_3$ | 1 | C$_6$H$_5$, H, 4-ClC$_6$H$_4$, 4-pyridyl |
| H | (CH$_2$)$_3$ | CH(CH$_3$) | 1 | C$_6$H$_5$, 4-FC$_6$H$_4$, 2-pyridyl |
| H | (CH$_2$)$_3$ | CH(CH$_3$)(CH$_2$)$_2$ | 1 | 4-pyridyl, H, 4-ClC$_6$H$_4$ |
| PE, H, CH$_3$ | CH(CH$_3$)(CH$_2$)$_2$ | — | 0 | C$_6$H$_5$, 4-pyridyl |
| H | CH(CH$_3$)(CH$_2$)$_2$ | (CH$_2$)$_2$ | 1 | C$_6$H$_5$, 4-FC$_6$H$_4$, 4-pyridyl |
| PE, H | CH(CH$_3$)(CH$_2$)$_2$ | (CH$_2$)$_4$ | 1 | C$_6$H$_5$, 4-pyridyl, H |
| H, CH$_3$ | CH(CH$_3$)(CH$_2$)$_2$ | CH(CH$_3$)(CH$_2$)$_2$ | 1 | C$_6$H$_5$, 4-ClC$_6$H$_4$, H |
| H | CH(CH$_3$)(CH$_2$)$_2$ | CH$_2$CH(C$_2$H$_5$) | 1 | C$_6$H$_5$ |
| H, CH$_3$ | CH(CH$_3$)(CH$_2$)$_3$ | (CH$_2$)$_4$ | 1 | C$_6$H$_5$, 4-FC$_6$H$_4$, 2-pyridyl |
| PE, H | CH(C$_2$H$_5$)(CH$_2$)$_2$ | — | 0 | C$_6$H$_5$, 4-pyridyl |
| PE | (CH$_2$)$_8$ | — | 0 | C$_6$H$_5$ |
| H | CH(C$_2$H$_5$)(CH$_2$)$_2$ | (CH$_2$)$_2$CH(CH$_3$) | 1 | C$_6$H$_5$, 4-FC$_6$H$_4$ |
| PE, H, CH$_3$ | (CH$_2$)$_4$ | — | 0 | C$_6$H$_5$, 4-FC$_6$H$_4$, 4-ClC$_6$H$_4$, 4-pyridyl |
| PE, CH$_3$ | (CH$_2$)$_4$ | CH$_2$ | 1 | C$_6$H$_5$, 4-FC$_6$H$_4$, 4-pyridyl, 3-pyridyl |
| CH$_3$ | (CH$_2$)$_4$ | CH(CH$_3$)CH$_2$ | 1 | C$_6$H$_5$, H, 2-pyridyl, 4-FC$_6$H$_4$ |
| H | (CH$_2$)$_4$ | (CH$_2$)$_5$ | 1 | C$_6$H$_5$, 4-pyridyl, 4-ClC$_6$H$_4$ |

PREPARATION J

3-(3-Hydroxyphenyl)-1-phenoxybutane

A solution of 3-(3-benzyloxyphenyl)-1-phenoxybutane (11.2 g., 33.5 mM) in a mixture of ethyl acetate (110 ml.), ethanol (110 ml.) and concentrated hydrochloric acid (0.7 ml.) is hydrogenated for 2 hours under 60 p.s.i. hydrogen in the presence of 10% palladium-on-carbon (1.5 g.). Removal of the catalyst by filtration and concentration of the filtrate gives an oil. The oil is purified by chromatography on silica gel (100 g.) and eluting with benzene-ethyl acetate consisting of 0–10% ethyl acetate. The middle fractions are combined and concentrated to give the title product as an oil.

PREPARATION K

1-Bromo-3-(3-methoxyphenyl)butane

A solution of phosphorous tribromide (5.7 ml., 0.06 mole) in ether (30 ml.) is added to a solution of 3-(3-methoxyphenyl)-1-butanol (25.8 g., 0.143 mole) in ether (20 ml.) at −5° C. to −10° C. and the reaction mixture stirred at −5° C. to −10° C. for 2.5 hours. It is then warmed to room temperature and stirred for an additional 30 minutes. The mixture is poured over ice (200 g.) and the resulting mixture extracted with ether (3×50 ml.). The combined extracts are washed with 5% sodium hydroxide solution (3×50 ml.), saturated sodium chloride solution (1×50 ml.) and dried (Na₂SO₄). Removal of the ether and vacuum distillation of the residue affords the title product.

The following compounds are prepared from the appropriate

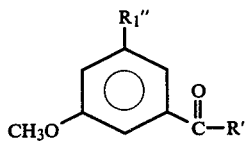

reactant wherein $R_1''$ is hydrogen or methyl and $R'$ is hydrogen, methyl or ethyl and the appropriate carbethoxyalkylidene triphenylphosphorane by the procedures of Preparations H, F, G and K.

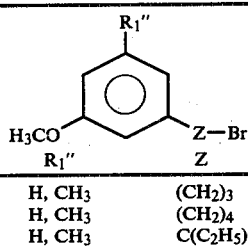

| $R_1''$ | Z |
|---|---|
| H, CH₃ | (CH₂)₃ |
| H, CH₃ | (CH₂)₄ |
| H, CH₃ | C(C₂H₅)CH₂ |

PREPARATION L

4-(3-Hydroxyphenyl)-1-(4-pyridyl)pentane

A mixture of 3-(3-methoxyphenyl)butyl triphenylphosphonium bromide (17.9 g., 35.4 mmoles) in dimethylsulfoxide (50 ml.) is added to 4-pyridinecarboxaldehyde (3.79 g., 35.4 mmoles) in tetrahydrofuran (40 ml.). The resulting mixture is then added dropwise to a slurry of 50% sodium hydride (1.87 g., 39 mmoles) in tetrahydrofuran (20 ml.) under a nitrogen atomosphere at 0°–5° C. Following completion of addition, the mixture is stirred for one hour at 0°–5° and then concentrated under reduced pressure. The concentrate is diluted with water (200 ml.) and then acidified with 6 N HCl. The aqueous acid solution is extracted with benzene (4×50 ml.). It is then made basic and extracted with ethyl acetate (3×50 ml.). Evaporation of the combined extracts after drying (MgSO₄) affords 4-(3-methoxyphenyl)-1-(4-pyridyl)-1-pentene as an oil.

Catalytic hydrogenation of the thus-produced pentene derivative in ethanol (250 ml.) using palladium-on-charcoal (1 g. of 10%) at 45 p.s.i. and concentrated hydrochloric acid (1 ml.) gives 4-(3-methoxyphenyl)-1-(4-pyridyl)pentane in quantitative yield.

The pentane derivative thus obtained is demethylated by heating a mixture of the compound (6.38 g., 25 mmoles) and pyridine hydrochloride (35 g.) under a nitrogen atmosphere at 210° C. for 8 hours. The hot mixture is poured into water (40 ml.) and the resulting solution made basic with 6 N sodium hydroxide. Water and pyridine are removed by distillation in vacuo. Ethanol (50 ml.) is added to the residue and the inorganic salts which precipitate are filtered off. The filtrate is concentrated in vacuo and the residue chromatographed on silica gel (150 g.) using as eluting agents 5% ethanol/benzene (4 liters), 10% ethanol/benzene (1 liter), 13% ethanol/benzene (1 liter) and 16% ethanol/benzene (5 liters). The product is isolated as a glassy solid by concentration of appropriate fractions of the eluate.

The 3-(3-methoxyphenyl)butyltriphenylphosphonium bromide is prepared by refluxing a mixture of 1-bromo-3-(3-methoxyphenyl)butane (19.09 g., 78.5 mmoles) and triphenyl phosphine (20.5 g., 78.5 mmoles) in xylene (60 ml.) for 18 hours. The reaction mixture is then cooled to room temperature and filtered. The filter cake is washed with ether and dried in a vacuum desicator to give the products.

Repetition of this procedure but using the appropriate bromo-(3-methoxyphenyl)alkane and the appropriate phenolic aldehyde or ketone affords the following compounds.

| $R_1''$ | Z | W |
|---|---|---|
| H, CH₃ | (CH₂)₃ | 2-pyridyl |
| H | (CH₂)₃ | 3-pyridyl |
| H, CH₃ | (CH₂)₃ | 4-pyridyl |
| H, CH₃ | (CH₂)₄ | 2-pyridyl |
| CH₃ | (CH₂)₄ | 4-pyridyl |
| H, CH₃ | CH₂CH(CH₃)CH₂ | 2-pyridyl |
| H | CH(CH₃)CH(CH₃)CH₂ | 3-pyridyl |
| H, CH₃ | CH(CH₃)CH(CH₃)CH₂ | 4-pyridyl |
| H, CH₃ | CH(CH₃)(CH₂)₃ | 3-pyridyl |
| H | CH(CH₃)CH(C₂H₅)CH₂ | 4-pyridyl |
| CH₃ | CH(C₂H₅)(CH₂)₂ | 4-pyridyl |
| H | CH(C₂H₅)(CH₂)₃ | 3-pyridyl |
| CH₃ | CH(C₂H₅)CH(C₂H₅)CH₂ | 4-pyridyl |
| CH₃ | (CH₂)₆ | C₆H₅ |
| CH₃ | (CH₂)₈ | C₆H₅ |
| H | CH(CH₃)(CH₂)₇ | C₆H₅ |
| H, CH₃ | CH(CH₃)(CH₂)₃ | 4-FC₆H₄ |
| H | C(CH₃)₂(CH₂)₃ | C₆H₅ |
| H | CH(CH₃)(CH₂)₃ | 4-ClC₆H₄ |
| CH₃ | CH(CH₃)(CH₂)₄ | 4-ClC₆H₄ |
| H | CH(CH₃)(CH₂)₂ | 4-FC₆H₄ |
| H, CH₃ | CH(CH₃)CH(CH₃)(CH₂)₅ | H |
| H, CH₃ | C(CH₃)₂(CH₂)₆ | H |
| H, CH₃ | (CH₂)₅ | H |

PREPARATION M

3-Methoxy-5-(2-phenylethenyl)acetophenone

Methyl lithium (501 ml. of a 2 molar solution, 1.00 M) is added over a period of 2.0 hours under a nitrogen atmosphere to a rapidly stirring solution of 5-methoxy-3-stilbene carboxylic acid (115.1 g., 0.50 M) in ether (200 ml.) - tetrahydrofuran (1200 ml.) at 15°–20° C. The reaction mixture is stirred for an additional hour at 15°-20° C. and then water (600 ml.) is slowly added while maintaining the temperature below 20° C. The aqueous phase is separated, extracted with ether (3×250 ml.) and the combined extracts washed with saturated brine (4×250 ml.) and then dried (Na$_2$SO$_4$). Concentration of the dried extract affords the title compound as an oil.

PREPARATION N

Following the procedures of Preparation F-I and L the compounds listed below are prepared from appropriate reactants and 3-methoxy-5-(2-phenylethenyl)acetophenone.

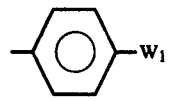

| Z | W |
| --- | --- |
| (CH$_2$)$_3$ | H |
| C(CH$_3$)$_2$(CH$_2$)$_6$ | H |
| CH(CH$_3$)CH(CH$_3$)(CH$_2$)$_5$ | H |
| CH(CH$_3$)(CH$_2$)$_3$ | C$_6$H$_5$ |
| (CH$_2$)$_{10}$ | H |
| CH(CH$_3$)(CH$_2$)$_3$ | 4-FC$_6$H$_4$ |
| C(CH$_3$)$_2$(CH$_2$)$_6$ | 4-ClC$_6$H$_4$ |
| CH(C$_2$H$_5$)CH$_2$ | C$_6$H$_5$ |
| CH(CH$_3$)(CH$_2$)$_3$ | 4-pyridyl |
| (CH$_2$)$_5$ | 2-pyridyl |
| (CH$_2$)$_5$ | H |
| (CH$_2$)$_8$ | C$_6$H$_5$ |
| CH(CH$_3$)(CH$_2$)$_2$CH(CH$_3$) | C$_6$H$_5$ |
| CH$_2$ | 4-ClC$_6$H$_4$ |
| (CH$_2$)$_3$—O— | C$_6$H$_5$ |
| (CH$_2$)$_3$—O—CH$_2$ | 4-FC$_6$H$_4$ |
| (CH$_2$)$_3$—O—CH(CH$_3$)(CH$_2$)$_2$ | C$_6$H$_5$ |
| CH(CH$_3$)(CH$_2$)$_2$—O—(CH$_2$)$_4$ | 4-pyridyl |
| (CH$_2$)$_3$—O—(CH$_2$)$_3$ | H |
| (CH$_2$)$_3$—O— | 4-FC$_6$H$_4$ |
| (CH$_2$)$_4$—O—CH$_2$ | 4-FC$_6$H$_4$ |
| CH(CH$_3$)(CH$_2$)$_2$—O—CH(CH$_3$) | C$_6$H$_5$ |
| CH(C$_2$H$_5$)(CH$_2$)$_2$—O— | C$_6$H$_5$ |
| (CH$_2$)$_4$—O— | H |
| (CH$_2$)$_8$O | C$_6$H$_5$ |
| (CH$_2$)$_3$OCH(CH$_3$)(CH$_2$)$_2$ | 4-pyridyl |
| (CH$_2$)$_7$ | H |
| C(CH$_3$)$_2$ | C$_6$H$_5$ |

What is claimed is:

1. A compound having the formula

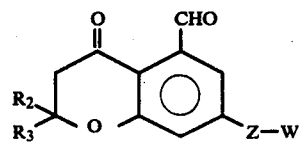

wherein each of R$_2$ and R$_3$ is selected from the group consisting of hydrogen and methyl;

Z is selected from the group consisting of
(a) alkylene having from one to ten carbon atoms;
(b) —(alk$_1$)$_m$-O-(alk$_2$)$_n$ - wherein each of (alk$_1$) and (alk$_2$) is alkylene having from one to ten carbon atoms, with the proviso that the summation of carbon atoms in (alk$_1$) plus (alk$_2$) is not greater than ten; each of m and n is 0 or 1; and W is selected from the group consisting of hydrogen, pyridyl,

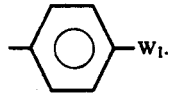

wherein W$_1$ is selected from the group consisting of hydrogen, fluoro and chloro.

2. A compound according to claim 1 wherein Z is —(alk$_1$)$_m$-O-(alk$_2$)$_n$ and W is

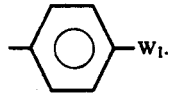

3. A compound according to claim 2 wherein Z is —O-(alk$_2$)—.

4. A compound according to claim 3 wherein O-(alk$_2$)- is —O-alkylene having from 5 to 9 carbon atoms.

5. A compound according to claim 4 wherein -O-(alk$_2$) is —O-CH(CH$_3$) (CH$_2$)$_3$-.

6. The compound according to claim 5 wherein each of R$_2$ and R$_3$ is methyl and W is

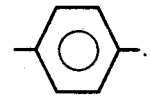

* * * * *

UNITED STATES PATENT AND TRADEMARK OFFICE
CERTIFICATE OF CORRECTION

PATENT NO. : 4,165,323
DATED : August 21, 1979
INVENTOR(S) : Johnson et al

It is certified that error appears in the above-identified patent and that said Letters Patent are hereby corrected as shown below:

Claim 6, line 3, the formula should read

--  --.

Signed and Sealed this

Thirteenth Day of November 1979

[SEAL]

Attest:

RUTH C. MASON
*Attesting Officer*

LUTRELLE F. PARKER
*Acting Commissioner of Patents and Trademarks*